United States Patent
Schaer

(10) Patent No.: US 6,811,544 B2
(45) Date of Patent: Nov. 2, 2004

(54) CATHETER POSITIONING SYSTEM

(76) Inventor: Alan K. Schaer, 5050 Elmgrove Ct., San Jose, CA (US) 95130

(*) Notice: Subject to any disclaimer, the term of this patent is extended or adjusted under 35 U.S.C. 154(b) by 81 days.

(21) Appl. No.: 10/313,736

(22) Filed: Dec. 6, 2002

(65) Prior Publication Data

US 2003/0083613 A1 May 1, 2003

Related U.S. Application Data

(63) Continuation of application No. 09/569,734, filed on May 11, 2000.
(60) Provisional application No. 60/133,807, filed on May 11, 1999.

(51) Int. Cl.[7] .................................................. A61M 31/00
(52) U.S. Cl. ........................ 604/95.04; 604/528; 606/41
(58) Field of Search .............................. 604/95.04, 523, 604/22, 105, 20, 528; 600/201, 101, 208, 585; 128/898; 606/7, 41; 607/123

(56) References Cited

U.S. PATENT DOCUMENTS

| | | |
|---|---|---|
| 4,441,286 A | 10/1983 | Cosman |
| 4,449,528 A | 5/1984 | Auth et al. |
| 4,522,205 A | 6/1985 | Taylor et al. |
| 4,569,801 A | 2/1986 | Molloy et al. |
| 4,641,649 A | 2/1987 | Walinsky et al. |
| 4,660,571 A | 4/1987 | Hess et al. |
| 4,662,368 A | 5/1987 | Hussein et al. |
| 4,672,962 A | 6/1987 | Hershenson |
| 4,673,563 A | 6/1987 | Berne et al. |
| 4,676,258 A | 6/1987 | Inokuchi et al. |
| 4,790,311 A | 12/1988 | Ruiz |
| 4,807,620 A | 2/1989 | Strul et al. |
| 4,924,863 A | 5/1990 | Sterzer |
| 4,936,281 A | 6/1990 | Stasz |
| 4,940,064 A | 7/1990 | Desai |

(List continued on next page.)

FOREIGN PATENT DOCUMENTS

| | | |
|---|---|---|
| EP | 0 472 368 A2 | 2/1992 |
| EP | 0 667 126 A1 | 8/1995 |
| EP | 0 711 573 A1 | 8/1995 |
| GB | 2 208 138 A | 3/1989 |
| WO | WO 93/00958 | 1/1993 |
| WO | WO 93/08755 | 5/1993 |
| WO | WO 93/166632 | 9/1993 |
| WO | WO 93/20767 | 10/1993 |
| WO | WO 93/20886 | 10/1993 |
| WO | WO 94/00050 | 1/1994 |

(List continued on next page.)

OTHER PUBLICATIONS

Hindricks, et al., "IX Nonpharmacologic Management Catheter Ablation," Current Management of Amythmias, pp. 373–378.

Helmut P. Weber et al., "Cardiovascular Application of the Nd: YAG Laser," Laser in Medicine and Surgery, 2:54–58, Mar. 8, 1988.

Helmut P. Weber et al., "Percutaneous Nd: YAG Laser Coagulation of Ventricular Myocardium in Dogs using a Special Electrode Laser Catheter," PACE, vol. 12, pp. 899–910, Jun. 1989.

(List continued on next page.)

Primary Examiner—Quang T. Van

(57) ABSTRACT

The present invention is a system adapted to position an ablation catheter at a location where a pulmonary vein extends from an atrium. The system includes a deflectable guidewire and a sheath. The ablation catheter is used with the positioning system, wherein the deflectable guidewire and the sheath cooperate so as to facilitate positioning of the catheter at the location.

22 Claims, 8 Drawing Sheets

U.S. PATENT DOCUMENTS

| | | | |
|---|---|---|---|
| 4,945,912 | A | 8/1990 | Langberg |
| 4,976,711 | A | 12/1990 | Parins et al. |
| 4,998,933 | A | 3/1991 | Eggers et al. |
| 5,035,694 | A | 7/1991 | Kasprzyk et al. |
| 5,078,717 | A | 1/1992 | Parins et al. |
| 5,078,736 | A | 1/1992 | Behl |
| 5,090,958 | A | 2/1992 | Sahota |
| 5,100,423 | A | 3/1992 | Fearnot |
| 5,104,393 | A | 4/1992 | Isner et al. |
| 5,147,355 | A | 9/1992 | Friedman et al. |
| 5,178,618 | A | 1/1993 | Kandarpa |
| 5,190,528 | A | 3/1993 | Fonger et al. |
| 5,190,540 | A | 3/1993 | Lee |
| 5,226,430 | A | 7/1993 | Spears et al. |
| 5,228,442 | A | 7/1993 | Imran |
| 5,231,984 | A | 8/1993 | Santana-Blank |
| 5,231,995 | A | 8/1993 | Desai |
| 5,255,679 | A | 10/1993 | Imran |
| 5,263,493 | A | 11/1993 | Avitall |
| 5,292,321 | A | 3/1994 | Lee |
| 5,293,869 | A | 3/1994 | Edwards |
| 5,295,484 | A | 3/1994 | Marcus et al. |
| 5,313,943 | A | 5/1994 | Houser et al. |
| 5,324,255 | A | 6/1994 | Passafaro et al. |
| 5,324,284 | A | 6/1994 | Imran |
| 5,341,807 | A | 8/1994 | Nardella |
| 5,342,292 | A | 8/1994 | Nita et al. |
| 5,344,435 | A | 9/1994 | Turner et al. |
| 5,345,936 | A | 9/1994 | Pomeranz et al. |
| 5,348,554 | A | 9/1994 | Imran et al. |
| 5,368,558 | A | 11/1994 | Nita |
| 5,370,678 | A | 12/1994 | Edwards et al. |
| 5,385,148 | A | 1/1995 | Lesh |
| 5,385,544 | A | 1/1995 | Edwards et al. |
| 5,391,197 | A | 2/1995 | Burdette et al. |
| 5,409,000 | A | 4/1995 | Imran |
| 5,423,808 | A | 6/1995 | Edwards et al. |
| 5,423,811 | A | 6/1995 | Imran et al. |
| 5,427,119 | A | 6/1995 | Swartz et al. |
| 5,433,708 | A | 7/1995 | Nichols et al. |
| 5,447,509 | A | 9/1995 | Mills et al. |
| 5,449,380 | A | 9/1995 | Chin |
| 5,456,682 | A | 10/1995 | Edwards et al. |
| 5,474,530 | A | 12/1995 | Passafaro et al. |
| 5,484,400 | A | 1/1996 | Edwards et al. |
| 5,487,385 | A | 1/1996 | Avitall |
| 5,497,119 | A | 3/1996 | Tedrow et al. |
| 5,497,774 | A | 3/1996 | Swartz et al. |
| 5,505,702 | A | 4/1996 | Amey |
| 5,505,730 | A | 4/1996 | Edwards |
| 5,522,873 | A | 6/1996 | Jackman et al. |
| 5,545,161 | A | 8/1996 | Imran |
| 5,545,193 | A | 8/1996 | Fleischman et al. |
| 5,549,661 | A | 8/1996 | Kordis et al. |
| 5,558,720 | A | 9/1996 | Sarraf et al. |
| 5,562,720 | A | 10/1996 | Stern et al. |
| 5,564,440 | A | 10/1996 | Swartz et al. |
| 5,571,088 | A | 11/1996 | Lennox et al. |
| 5,575,766 | A | 11/1996 | Swartz et al. |
| 5,575,772 | A | 11/1996 | Lennox |
| 5,575,788 | A | 11/1996 | Baker et al. |
| 5,575,810 | A | 11/1996 | Swanson et al. |
| 5,582,609 | A | 12/1996 | Swanson et al. |
| 5,588,432 | A | 12/1996 | Crowley |
| 5,606,974 | A | 3/1997 | Castellano et al. |
| 5,607,422 | A | 3/1997 | Smeets et al. |
| 5,617,854 | A | 4/1997 | Munsif |
| 5,630,837 | A | 5/1997 | Crowley |
| 5,642,736 | A | 7/1997 | Avitall |
| 5,645,082 | A | 7/1997 | Sung et al. |
| 5,655,548 | A | * 8/1997 | Nelson et al. ............... 128/898 |
| 5,658,278 | A | 8/1997 | Imran et al. |
| 5,673,695 | A | 10/1997 | McGee et al. |
| 5,676,662 | A | 10/1997 | Fleischhacker et al. |
| 5,683,445 | A | 11/1997 | Swoyer |
| 5,685,322 | A | 11/1997 | Sung et al. |
| 5,685,839 | A | 11/1997 | Edwards et al. |
| 5,687,723 | A | 11/1997 | Avitall |
| 5,687,729 | A | 11/1997 | Schaetzle |
| 5,688,267 | A | 11/1997 | Panescu et al. |
| 5,690,611 | A | 11/1997 | Swartz et al. |
| 5,693,078 | A | 12/1997 | Desai et al. |
| 5,697,925 | A | 12/1997 | Taylor |
| 5,697,927 | A | 12/1997 | Imran et al. |
| 5,702,438 | A | 12/1997 | Avitall |
| 5,715,818 | A | 2/1998 | Swartz et al. |
| 5,716,389 | A | 2/1998 | Walinsky et al. |
| 5,718,231 | A | 2/1998 | Dewhurst et al. |
| 5,718,241 | A | 2/1998 | Ben-Haim et al. |
| 5,718,701 | A | 2/1998 | Shai et al. |
| 5,720,775 | A | 2/1998 | Larnard |
| 5,722,400 | A | 3/1998 | Ockuly et al. |
| 5,722,401 | A | 3/1998 | Pietroski et al. |
| 5,722,403 | A | 3/1998 | McGee et al. |
| 5,722,963 | A | 3/1998 | Lurie et al. |
| 5,725,494 | A | 3/1998 | Brisken |
| 5,725,512 | A | 3/1998 | Swartz et al. |
| 5,728,062 | A | 3/1998 | Brisken |
| 5,730,127 | A | 3/1998 | Avitall |
| 5,730,704 | A | 3/1998 | Avitall |
| 5,733,315 | A | 3/1998 | Burdette et al. |
| 5,735,280 | A | 4/1998 | Sherman et al. |
| 5,735,811 | A | 4/1998 | Brisken |
| 5,735,846 | A | 4/1998 | Panescu et al. |
| 5,741,249 | A | 4/1998 | Moss et al. |
| 5,741,320 | A | 4/1998 | Thornton et al. |
| 5,743,870 | A | 4/1998 | Edwards |
| 5,743,903 | A | 4/1998 | Stern et al. |
| 5,755,663 | A | 5/1998 | Larsen et al. |
| 5,755,664 | A | 5/1998 | Rubenstein |
| 5,755,715 | A | 5/1998 | Stern et al. |
| 5,755,760 | A | 5/1998 | Maguire et al. |
| 5,769,846 | A | 6/1998 | Edwards et al. |
| 5,782,239 | A | 7/1998 | Webster, Jr. |
| RE35,880 | E | 8/1998 | Waldman et al. |
| 5,797,877 | A | 8/1998 | Hamilton et al. |
| 5,797,903 | A | 8/1998 | Swanson et al. |
| 5,797,905 | A | 8/1998 | Fleischman et al. |
| 5,800,378 | A | 9/1998 | Edwards et al. |
| 5,800,379 | A | 9/1998 | Edwards |
| 5,800,413 | A | 9/1998 | Swartz et al. |
| 5,800,428 | A | 9/1998 | Nelson et al. |
| 5,800,429 | A | 9/1998 | Edwards |
| 5,807,249 | A | 9/1998 | Qin et al. |
| 5,807,308 | A | 9/1998 | Edwards |
| 5,807,391 | A | 9/1998 | Wijkamp |
| 5,807,395 | A | 9/1998 | Mulier et al. |
| 5,820,591 | A | * 10/1998 | Thompson et al. ............ 604/95 |
| 5,840,031 | A | 11/1998 | Crowley |
| 5,840,076 | A | 11/1998 | Swanson et al. |
| 5,843,154 | A | 12/1998 | Osypka |
| 5,846,218 | A | 12/1998 | Brisken et al. |
| 5,860,920 | A | 1/1999 | McGee et al. |
| 5,860,974 | A | 1/1999 | Abele |
| 5,861,021 | A | 1/1999 | Thome et al. |
| 5,899,896 | A | 5/1999 | Arless et al. |
| 5,971,983 | A | 10/1999 | Lesh |
| 6,012,457 | A | * 1/2000 | Lesh ........................ 128/898 |
| 6,023,638 | A | 2/2000 | Swanson |
| 6,024,740 | A | 2/2000 | Lesh et al. |
| 6,064,902 | A | 5/2000 | Haissaguerre et al. |

| | | | |
|---|---|---|---|
| 6,071,279 A | | 6/2000 | Whayne et al. |
| 6,071,281 A | | 6/2000 | Burnside et al. |
| 6,117,101 A | | 9/2000 | Diederich et al. |
| 6,179,809 B1 | | 1/2001 | Khairkhahan et al. |
| 6,237,605 B1 | | 5/2001 | Vaska et al. |
| 6,254,599 B1 | * | 7/2001 | Lesh et al. .................. 606/41 |
| 6,332,880 B1 | * | 12/2001 | Yang et al. .................. 604/528 |

FOREIGN PATENT DOCUMENTS

| | | |
|---|---|---|
| WO | WO 94/21165 | 9/1994 |
| WO | WO 94/21167 | 9/1994 |
| WO | WO 94/21168 | 9/1994 |
| WO | WO 95/10318 | 4/1995 |
| WO | WO 95/10319 | 4/1995 |
| WO | WO 95/10321 | 4/1995 |
| WO | WO 95/00036 | 1/1996 |
| WO | WO 96/10981 | 4/1996 |
| WO | WO 96/26724 | 6/1996 |
| WO | WO 96/26675 | 9/1996 |
| WO | WO 96/32885 | 10/1996 |
| WO | WO 96/32897 | 10/1996 |
| WO | WO 97/32525 | 9/1997 |
| WO | WO 97/37607 | 10/1997 |
| WO | WO 97/45156 | 12/1997 |
| WO | WO 98/02201 | 1/1998 |
| WO | WO 99/00064 | 1/1999 |

OTHER PUBLICATIONS

Diederich, et al., Induction of Hyperthemia using an Intracavitary Multielement Ultrasonic Applicator. Transactions In Biomedical Engineering, vol. 36, No. 4 Apr. 1989.

Diederich, et. al., The Development of Intracavitary Ultrasonic Applicators for Hyperthemia: A Design and Experimental Study, Medical Physics, Jul./Aug. 1990.

McMath, et. al., "Percutaneous Laser Balloon Coagulation of Accessory Pathways," Diagnostic and Therapeutic Cardiovascular Interventions, 1991.

Cox, et al., "The Surgical Treatment of Atrial Fibrillation: I. Summary of the current concepts of the mechanisms of atrial flutter and atrial fibrillation," The Journal of Thoracic and Cardiovascular Surgery, pp. 402–405, 1991.

Cox, et al., "The surgical treatment of atrial fibrillation: IV Surgical Technique, "The Journal Thoracic and Cardiovascular Surgery, pp. 584–592, 1991.

Schuger, et al., "Long Term Effects of Percutaneous Laser Balloon Ablation from the Canine Coronary Sinus," Circulation, vol. 86, No. 3, Sep. 1992.

Avitall, et al., "Physics and Engineering of Transcatheter Cardiac Tissue Ablation." JACC, vol. 22, No. 3, Sep. 1993.

Jais, et al., "Biatrial Dimensions Relevant to Catheter Ablation," NASPE 17th Annual Scientific Sessions Abstract Forum, Dec. 1995.

Fram, et. al., "feasibility of Radiofrequency Powered, Thermal Balloon Ablation of Atrioventricular Bypass Tracts Via the Coronary Sinus; In Vivo Canine Studies, "Pace, vol. 18, pp. 1518–1530, Aug. 1995.

Sueda, et. al., "Simple left atrial fibrillation associated with mitral valve disease," Ann Thorac Surg 62:1796–1800 (1996).

Haissaguerre et. al., "Right and Left Atrial Radiofrequency Catheter Therapy of Paroxysmal Atrial Fibrillation", Journall of Cardiovascular Electrophysiology, vol. 7, No. 12, pp. 1132–1144, Dec. 1996.

Helmut P. Weber et al., "Laser versus Radiofrequency Catheter Ablation of Ventricular Myocardium in Dogs: A Comparitive Test, "Cardiology, 88:346–352, 1997.

Helmut P. Weber et al., "Laser Coagulation of Atrial Myocardium for Ablation of Atrioventricular Nodal Reentrant Tachycardia," European Heart Journal, vol. 18, pp. 487–495, 1997.

J. Borbola, "Transcatheter Laser Ablation of Atrioventricular Nodal Reentrant Tachycardia–Do We Really Need a Newer Energy Source?, "European Heart Journal, vol. 18, pp. 357–358, 1997.

Jais, et. al., "A Focal Source of Atrial Fibrillation Treated by Discrete Radiofrequency Ablation," Circulation, vol. 95, No. 3 pp. 572–576, Feb. 4, 1997.

Helmut P. Weber et al., "Transcatheter Endomyocardial Laser Revascularization: A Feasability Test," The Thoracic and Cardiovascular Surgeon, vol. 46, pp. 74–76, Apr. 1998.

* cited by examiner

CATHETER POSITIONING SYSTEM

RELATED APPLICATIONS

This application is a Continuation of U.S. application Ser. No. 09/569,734 filed on May 11, 2000, to which this application claims priority under 35 U.S.C. §120. This application also claims priority under 35 U.S.C. §119(e) to Provisional Application No. 60/133,807, filed on May 11, 1999.

BACKGROUND OF THE INVENTION

1. Field of the Invention

The present invention relates to a system adapted to position an ablation catheter at a location where a pulmonary vein extends from the left atrium.

2. Description of the Related Art

Cardiac arrhythmia's, particularly atrial fibrillation, are a pervasive problem in modem society. Although many individuals lead relatively normal lives despite persistent atrial fibrillation, the condition is associated with an increased risk of myocardial ischemia, especially during strenuous activity. Furthermore, persistent atrial fibrillation has been linked to congestive heart failure, stroke, and other thromboembolic events. Thus, atrial fibrillation is a major public health problem.

Normal cardiac rhythm is maintained by a cluster of pacemaker cells, known as the sinoatrial ("SA") node, located within the wall of the right atrium. The SA node undergoes repetitive cycles of membrane depolarization and repolarization, thereby generating a continuous stream of electrical impulses, called "action potentials." These action potentials orchestrate the regular contraction and relaxation of the cardiac muscle cells throughout the heart. Action potentials spread rapidly from cell to cell through both the right and left atria via gap junctions between the cardiac muscle cells. Atrial arrhythmia's result when electrical impulses originating from sites other than the SA node are conducted through the atrial cardiac tissue.

In most cases, atrial fibrillation results from perpetually wandering reentrant wavelets, which exhibit no consistent localized region(s) of aberrant conduction. Alternatively, atrial fibrillation may be focal in nature, resulting from rapid and repetitive changes in membrane potential originating from isolated centers, or foci, within the atrial cardiac muscle tissue. These foci exhibit consistent centrifugal patterns of electrical activation, and may act as either a trigger of atrial fibrillatory paroxysmal or may even sustain the fibrillation. Recent studies have suggested that focal arrhythmia's often originate from a tissue region along the pulmonary veins of the left atrium, and even more particularly in the superior pulmonary veins.

Several surgical approaches have been developed for the treatment of atrial fibrillation. For example, Cox, J L et al. disclose the "maze" procedure, in "The Surgical Treatment Of Atrial Fibrillation. I. Summary", *Thoracic and Cardiovascular Surgery* 101(3):402–405 (1991) and "The Surgical Treatment Of Atrial Fibrillation. IV. Surgical Technique", *Thoracic and Cardiovascular Surgery* 101(4):584–592 (1991). In general, the maze procedure is designed to relieve atrial arrhythmia by restoring effective SA node control through a prescribed pattern of incisions about the cardiac tissue wall. Although early clinical studies on the maze procedure included surgical incisions in both the right and left atrial chambers, more recent reports suggest that the maze procedure may be effective when performed only in the left atrium (see for example Sueda et al., "Simple Left Atrial Procedure For Chronic Atrial Fibrillation Associated With Mitral Valve Disease" (1996)).

The left atrial maze procedure involves forming vertical incisions from the two superior pulmonary veins and terminating in the region of the mitral valve annulus, traversing the inferior pulmonary veins en route. An additional horizontal incision connects the superior ends of the two vertical incisions. Thus, the atrial wall region bordered by the pulmonary vein ostia is isolated from the other atrial tissue. In this process, the mechanical sectioning of atrial tissue eliminates the atrial arrhythmia by blocking conduction of the aberrant action potentials.

The moderate success observed with the maze procedure and other surgical segmentation procedures have validated the principle that mechanically isolating cardiac tissue may successfully prevent atrial arrhythmia's, particularly atrial fibrillation, resulting from either perpetually wandering reentrant wavelets or focal regions of aberrant conduction. Unfortunately, the highly invasive nature of such procedures may be prohibitive in many cases. Consequently, less invasive catheter-based approaches to treat atrial fibrillation through cardiac tissue ablation have been developed.

These less invasive catheter-based therapies generally involve introducing a catheter within a cardiac chamber, such as in a percutaneous translumenal procedure, wherein an energy sink on the catheter's distal end portion is positioned at or adjacent to the aberrant conductive tissue. Upon application of energy, the targeted tissue is ablated and rendered non-conductive.

The catheter-based methods can be subdivided into two related categories, based on the etiology of the atrial arrhythmia. First, focal arrhythmias have proven amenable to localized ablation techniques, which target the foci of aberrant electrical activity. Accordingly, devices and techniques have been disclosed which use end-electrode catheter designs for ablating focal arrhythmia's centered in the pulmonary veins, using a point source of energy to ablate the locus of abnormal electrical activity. Such procedures typically employ incremental application of electrical energy to the tissue to form focal lesions.

The second category of catheter-based ablation methods is designed for treatment of the more common forms of atrial fibrillation, resulting from perpetually wandering reentrant wavelets. Such arrhythmias are generally not amenable to localized ablation techniques, because the excitation waves may circumnavigate a focal lesion. Thus, the second class of catheter-based approaches have generally attempted to mimic the earlier surgical segmentation techniques, such as the maze procedure, wherein continuous linear lesions are required to completely segment the atrial tissue so as to block conduction of the reentrant wave fronts.

For the purpose of comparison, ablation catheter devices and related methods have also been disclosed for the treatment of ventricular or supraventricular tachycardias, such as disclosed by Lesh, M D in "Interventional Electrophysiology—State Of The Art, 1993" *American Heart Journal,* 126:686–698 (1993) and U.S. Pat. No. 5,231,995 to Desai.

While feasible catheter designs for imparting linear ablation tracks have been described, as a practical matter, most of these catheter assemblies have been difficult to position and maintain placement and contact pressure long enough and in a sufficiently precise manner in the beating heart to successfully form segmented linear lesions along a chamber wall. Indeed, many of the aforementioned methods have generally failed to produce closed transmural lesions, thus leaving the opportunity for the reentrant circuits to reappear in the gaps remaining between point or drag ablations. In addition, minimal means have been disclosed in these embodiments for steering the catheters to anatomic sites of interest such as the pulmonary veins.

None of the catheter-based ablation assemblies disclose a system adapted for positioning one end of a linear ablation element within a first ostium of a first pulmonary vein and the other end of the ablation element within a second ostium of a second pulmonary vein. Nor does the prior art disclose a method for securing the ablation element between a first and second anchor, thereby maintaining a desired linear position in contact with the atrial wall and facilitating the formation of a linear ablation track along the length of tissue between the anchors.

SUMMARY OF THE INVENTION

The present invention relates to a positioning system for guiding a catheter to a location where a pulmonary vein extends from an atrium. The system comprises a deflectable guidewire, a sheath and a catheter. The deflectable guidewire is adapted for slidable advancement through the sheath, and has a deflectable distal end so that it can be steered into a position for engagement with a pulmonary vein. The catheter is adapted for advancement over the deflectable guidewire and into the atrium.

In accordance with this mode, the deflectable guidewire comprises a wire wound coil surrounding a moveable pullwire.

In one variation of the positioning system, the deflection guidewire is integral with the catheter. The catheter preferably comprises proximal and distal ends and a moveable pullwire attached to the distal end of the catheter. The proximal end of the catheter is adapted to facilitate manipulation of the pullwire, such that manipulation of the pullwire causes deflection of the distal end of the catheter.

In a variation to the present mode, the catheter comprises an electrode element. The electrode element may be a mapping electrode, an ablation electrode, or both a mapping electrode and an ablation electrode. In one mode, the electrode element may be an RF ablation element.

Where the catheter comprises an ablation element, the ablation element may be selected from the group consisting of a microwave ablation element, a cryogenic ablation element, a thermal ablation element, a light-emitting ablation element, and an ultrasound transducer. The ablation element may be adapted to form a linear lesion, a circumferential lesion, or both.

In a variation to this mode, the guidewire may be selected from the group consisting of a guidewire, an anchor wire, and a deflectable guidewire. The anchor wire comprises an elongate body with proximal and distal end portions and having an expandable member along the distal end portion, such that radial expansion of the expandable member is adapted to anchor the guidewire within the pulmonary vein.

In accordance with another mode of the present invention, a positioning system is disclosed for guiding an ablation catheter to a location where a lumen extends from a body cavity. The positioning system comprises a deflectable guidewire and a transeptal sheath. The deflectable guidewire device is adapted to be removably engaged within the sheath, whereby the sheath and deflectable cooperate to facilitate positioning of the ablation catheter at the location when the catheter is advanced through the sheath and into the body cavity and guided toward the location.

In a variation to this mode, the deflectable guidewire is integral with the catheter, wherein the catheter further comprises proximal and distal ends and a moveable pullwire attached to the distal end of the catheter, and wherein the proximal end of the catheter is adapted to facilitate manipulation of the pullwire, such that manipulation of the pullwire causes deflection of the distal end of the catheter.

The ablation catheter comprises an ablation element, which may be selected from the group consisting of a microwave ablation element, a cryogenic ablation element, a thermal ablation element, a light-emitting ablation element, and an ultrasound transducer. The ablation element may be adapted to form a linear lesion, a circumferential lesion, or both.

In accordance with another mode of the present invention, a positioning system is disclosed for guiding an ablation catheter to a location where a pulmonary vein extends from an atrium. The system comprises a deflection device and a transeptal sheath having proximal and distal ends, wherein the deflection device is removably positionable within the transeptal sheath without extending beyond the distal end of the sheath.

In a variation to this mode of the invention, the deflection device comprises a pre-shaped stylet. In addition or in the alternative, the deflection device may comprise a pre-shaped tubular guide member.

In another variation of the positioning system, the deflection device is integral with the sheath. The sheath preferably comprises proximal and distal ends and a moveable pullwire attached to the distal end of the sheath. The proximal end of the sheath is adapted to facilitate manipulation of the pullwire, such that manipulation of the pullwire causes deflection of the distal end of the sheath.

In another variation of the positioning system, the deflection device is integral with the catheter, wherein the catheter further comprises proximal and distal ends and a moveable pullwire attached to the distal end of the catheter, and wherein the proximal end of the catheter is adapted to facilitate manipulation of the pullwire, such that manipulation of the pullwire causes deflection of the distal end of the catheter.

In another variation of the present mode, the catheter comprises an electrode element. The electrode element may be a mapping electrode, an ablation electrode, or both a mapping electrode and an ablation electrode. In one mode, the electrode element may be an RF ablation element.

Where the catheter comprises an ablation element, the ablation element may be selected from the group consisting of a microwave ablation element, a cryogenic ablation element, a thermal ablation element, a light-emitting ablation element, and an ultrasound transducer. The ablation element may be adapted to form a linear lesion, a circumferential lesion, or both.

DETAILED DESCRIPTION OF THE PREFERRED EMBODIMENT

Figure 1:
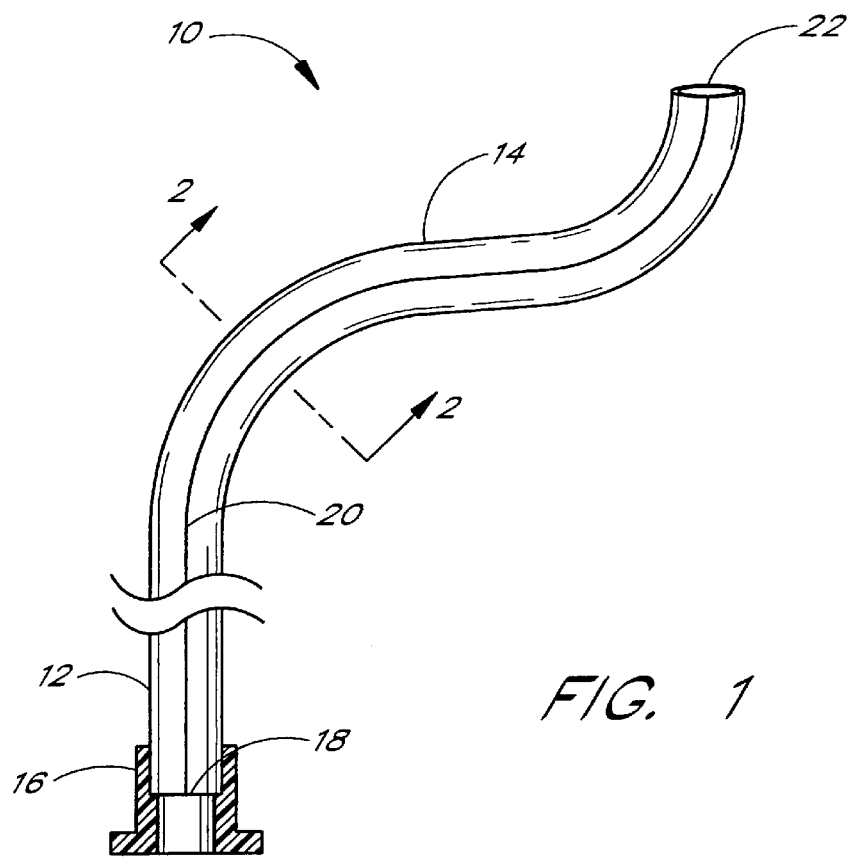
FIG. 1 is a perspective view of a variation of the guiding introducer of the present invention in which the introducer has a slit that extends along the entire length of the tubular member.
Figure 2A:
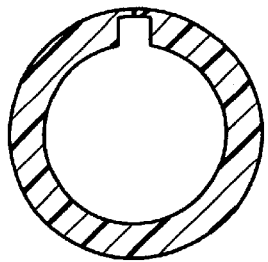
FIGS. 2A–D are transverse cross-sectional views, taken along line 2—2, showing various configurations for the longitudinal slit.
Figure 2B:
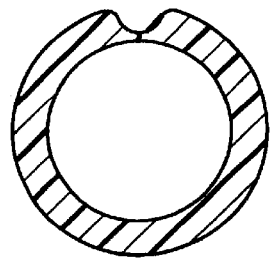
Figure 2C:
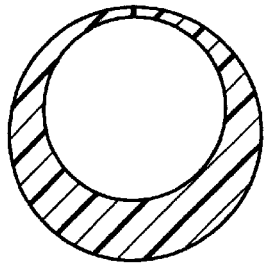
Figure 2D:
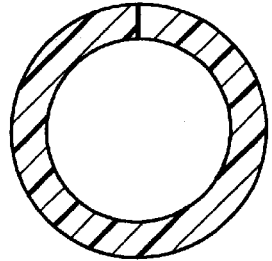

The invention relates to a system for positioning an ablation catheter within the left atrium. More specifically, the positioning system of the present invention is adapted to position and anchor the distal end of an ablation element within the first ostium of a first pulmonary vein and the proximal end of the ablation element within the second ostium of a second pulmonary vein. Preferably, the system includes a transeptal sheath inserted through an atrial septum that separates a right atrium from a left atrium. In one variation, a guiding introducer slideably engaged within the transeptal sheath has a preshaped distal portion adapted to point toward the first ostium of the first pulmonary vein. The preferred positioning system also incorporates a balloon anchor wire that is advanced through the preshaped guiding introducer and into the first pulmonary vein. The balloon anchor wire is anchored within the pulmonary vein by inflating a balloon on the distal end of the balloon anchor wire. The preshaped guiding introducer can then be retracted and removed from the balloon anchor wire by sliding off the proximal end or in a variation, by peeling away from the balloon anchor wire.

Alternatively, the balloon anchor wire may be replaced by a conventional guidewire or preferably, a deflectable guidewire adapted to permit the user to control the deflection of the distal portion, such that the deflectable guidewire can be advanced and steered into position for engaging the first pulmonary vein. The deflectable guidewire may be inserted either directly through the transeptal sheath or through a preshaped guiding introducer slideably engaged in the transeptal sheath. Deflection of the distal portion of the guidewire, once within the first pulmonary vein, may serve to anchor the guidewire within the pulmonary vein. In this case, the deflectable guidewire would take the place of the balloon anchor wire described above.

The ablation catheter in accordance with the present invention has an ablation element with an ablation length extending proximally from the distal portion of the ablation catheter. The ablation catheter is adapted to slideably engage the balloon anchor wire or the deflectable guidewire within an internal passageway or an external sleeve, the guidewire tracking means having a distal port located distal to the distal end of an ablation element. The ablation catheter may be introduced into the left atrium by tracking over the balloon anchor wire or the deflectable guidewire, whereby advancing the ablation catheter over the balloon anchor wire or the deflectable guidewire causes the distal end of the ablation element to engage the first pulmonary vein.

The ablation catheter preferably also has a second guidewire tracking means, comprising either an internal passageway or an external sleeve, with a second port located proximal to the proximal end of the ablation element. In one variation, a second guidewire preloaded and slideably engaged within the second guidewire passageway of the ablation catheter may be advanced directly out of the second guidewire port and into the second pulmonary vein.

Preferably, a second preshaped guiding introducer, preloaded and slideably engaged within the second guidewire passageway of the ablation catheter is advanced out of the proximal guidewire port and positioned in such a manner as to direct the second guidewire, slideably engaged within the guiding introducer, toward the second pulmonary vein. The second guiding introducer may optionally be advanced into the ostium of the second pulmonary vein, thereby insuring that the second guidewire cannulates the vein.

Alternatively, a steerable, deflectable guidewire may be preloaded and slideably engaged within the second guidewire passageway in the ablation element. In this variation, the proximal end of the deflectable guidewire is adapted to permit the user to control the deflection of the distal portion, such that the deflectable guidewire can be advanced and steered into position for engaging the second pulmonary vein. Deflection of the distal portion of the deflectable guidewire once within the second pulmonary vein may anchor the guidewire and thereby provide a better placement of the proximal end of the ablation element.

In another embodiment, the second guidewire may be fed into the second pulmonary vein prior to introducing the ablation catheter. A second guiding introducer with a preshaped distal end adapted to point toward the second pulmonary vein may be used to advance the second guidewire into the pulmonary vein. Where a balloon anchor wire and a guidewire have been positioned within the respective first and second pulmonary veins, the ablation catheter may then be inserted over the two wires and fed into the left atrium through the transeptal sheath. Advancing the distal portion of the ablation catheter over the balloon anchor wire, which is anchored within the first pulmonary vein, causes the distal end of the ablation element to be positioned within and anchored to the first ostium of the first pulmonary vein. Further advancing the ablation catheter over the second guidewire which is located within the second pulmonary vein causes the proximal end of the ablation element to engage the second ostium of the second pulmonary vein, thereby securing the ablation length against the atrial wall between the first and second pulmonary vein ostia.

It is contemplated that the subject matter disclosed herein may be combined with various embodiments which have formed the subject matter of other contemporaneous or previous patent filings, including without limitation the embodiments shown and described in the following issued patents and filed provisional and non-provisional U.S. Patent Applications:

(1) U.S. patent application Ser. No. 08/853,861 filed May 9, 1997 for "Tissue Ablation Device And Method Of Use", now U.S. Pat. No. 5,971,983;
(2) U.S. patent application Ser. No. 08/889,798 filed Jul. 8, 1997 for "Circumferential Ablation Device Assembly", now U.S. Pat. No. 6,024,740;
(3) U.S. patent application Ser. No. 08/889,835 filed Jul. 8, 1997 for "Device And Method For Forming A Circumferential Conduction Block In A Pulmonary Vein", now U.S. Pat. No. 6,012,457;
(4) U.S. patent application Ser. No. 09/073,907 filed May 6, 1998 for "Tissue Ablation Device With Fluid Irrigated Electrode";
(5) U.S. patent application Ser. No. 09/199,736 filed Nov. 25, 1998 for "Circumferential Ablation Device Assembly";
(6) U.S. patent application Ser. No. 09/240,068 filed Jan. 29, 1999 for "Device And Method For Forming A Circumferential Conduction Block In A Pulmonary Vein";
(7) U.S. patent application Ser. No. 09/260,316 filed Mar. 1, 1999 for "Tissue Ablation System And Method For Forming Long Linear Lesion";
(8) Provisional U.S. Application No. 60/122,571, Filed on Mar. 2, 1999 for "Feedback Apparatus And Method For Ablation At Pulmonary Vein Ostium";
(9) Provisional U.S. Application No. 60/125,509, filed Mar. 19, 1999 for "Circumferential Ablation Device Assembly And Methods Of Use And Manufacture Providing An Ablative Circumferential Band Along An Expandable Member";
(10) Provisional U.S. Application No. 60/125,928, filed Mar. 23, 1999 for "Circumferential Ablation Device Assembly And Methods Of Use And Manufacture Providing An Ablative Circumferential Band Along An Expandable Member";
(11) Provisional U.S. Application No. 60/133,610, filed May 11, 1999 for "Balloon Anchor Wire";
(12) Provisional U.S. Application No. 60/133,680, filed May 11, 1999 for "Apparatus And Method Incorporating An Ultrasound Transducer";
(13) Provisional U.S. Application No. 60/133,677, filed May 11, 1999 for "Tissue Ablation Device Assembly And Method For Electrically Isolating A Pulmonary Vein Ostium From A Posterior Left Atrial Wall";
the disclosures of these references are herein incorporated in their entirety by reference.

Preshaped Guiding Introducer

With reference to FIG. 1, there is shown a perspective view of a "peel-away" variation of the guiding introducer 10. The guiding introducer 10 consists of a tubular member 12 with a preshaped distal region 14 and a removable hub 16 on the proximal end 18 of the tubular member. The tubular member 12 has a slit 20 that extends along the entire length of the tubular member. The distal region 14 of the guiding introducer is preshaped so that the distal orifice 22 can be positioned to point toward a selected pulmonary vein by adjustably advancing and retracting the guiding introducer 10 through a transeptal sheath and by torquing the proximal end 18 of the guiding introducer.

The guiding introducer in accordance with the present invention may have any shape consistent with the purpose of the guiding introducer to direct a guidewire toward a predetermined pulmonary vein. Once the guidewire has been placed in the pulmonary vein, the guiding introducer shown in FIG. 1 is adapted to be peeled away from the guidewire by removing the proximal hub and opening the tubular member along the longitudinal slit 20. FIGS. 2A–D are transverse cross-sectional views, taken along line 2—2, showing various configurations for the longitudinal slit. In other embodiments, the guiding introducer can be retracted and removed from the coaxially engaged guidewire by sliding off the proximal end of the guidewire.

The tubular member, or parts thereof, could be fashioned from a wide variety of polymeric materials including, polyimide, nylon, Pebax, polyethylene, or PVC. The proximal shaft could be made from stiffer materials such as nickel titanium or stainless steel. The shaft could be of composite construction, incorporating braided strands that help provide torque transmission. Such strands could consist of materials including flat or round metallic wire (i.e., stainless steel), Dacron and Kevlar.

The tubular guiding introducer may have a permanently mounted luer on the proximal end that allows easy front-loading of the guidewire and flushing of the lumen. However, backloading of the ablation catheter over the guiding introducer may be preferred, requiring a removable (or none at all) proximal hub or adapter, as illustrated in FIG. 1. Such a removable hub or adapter could consist of a luer with collapsible O-ring seal.

Dimensions of the device would depend on the guidewire being accommodated. Typical guidewires to be used would range in diameter from about 0.014" to 0.038". The interior lumen typically adds about 0.004" to 0.010" to these sizes. Wall thicknesses could range from about 0.002" to 0.012". Device length would range from about 90 cm to about 300 cm depending on the need for backloading the catheter device over the guiding introducer. The outer diameter of the guiding introducer is approximately 5–10 F, preferably about 7 F, thereby permitting the guiding introducer to enter the left atrium by sliding within a transeptal sheath. Where the guiding introducer is to be employed for guiding the second guidewire into the second pulmonary vein, the outer diameter of the guiding introducer is preferably about 4–5 F, thereby permitting the guiding introducer to slide within the second guidewire passageway in the ablation catheter and exit the ablation catheter via the second guidewire port.

Figure 3:
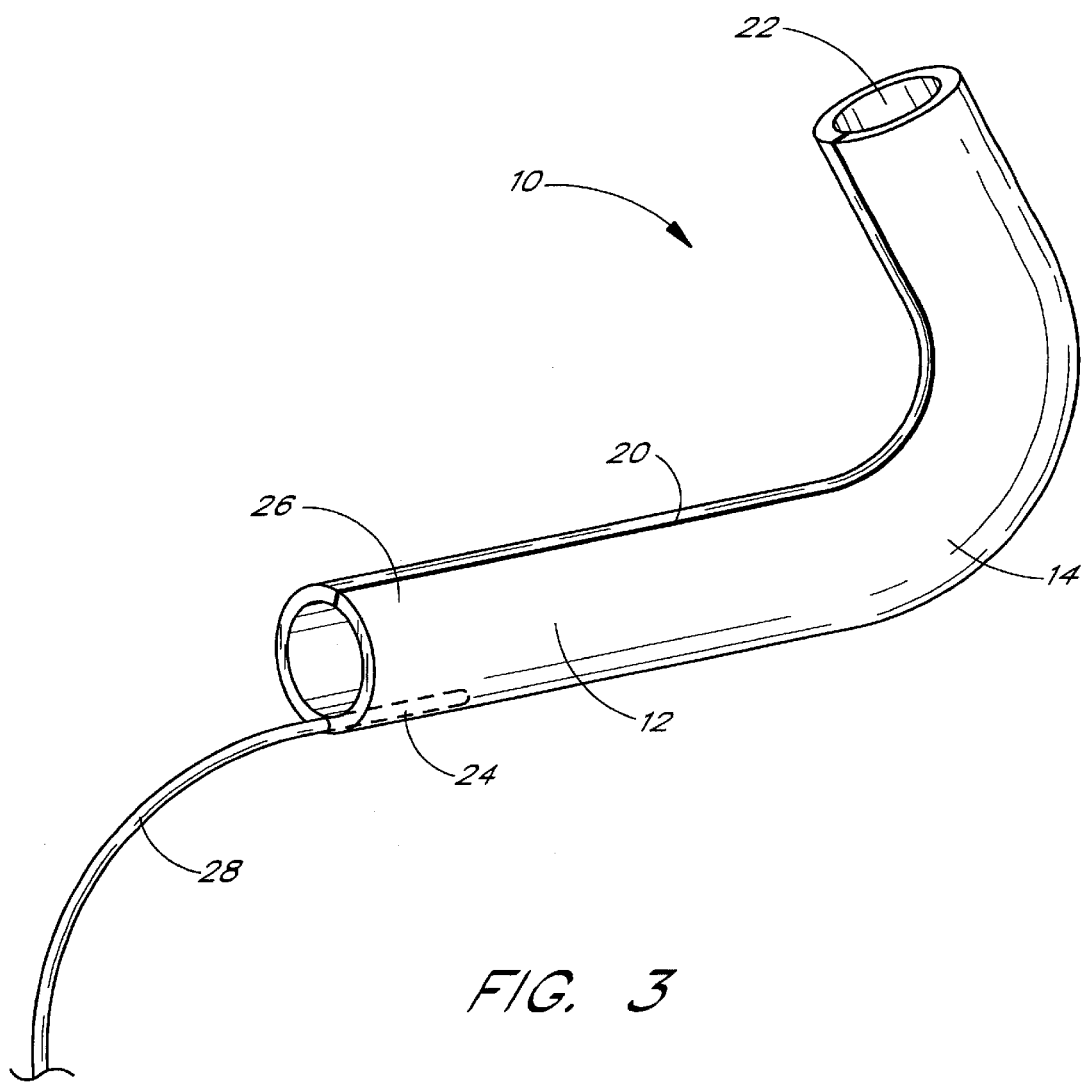
FIG. 3 is a perspective view of a variation of the peel-away guiding introducer, in which the guiding introducer is mounted on the distal end of a mandrel.

With reference to FIG. 3, there is shown another variation of a peel-away guiding introducer of the present invention in which a monorail guide system is employed. The proximal end 26 of the tubular member 12 is secured to the distal end 24 of a mandrel or hypotube 28. As described above with reference to FIG. 1, the distal region 14 is preshaped to point toward a predetermined site and the tubular member has a longitudinal slit 20 to facilitate peel-away removal. The guiding introducer 10, preloaded with a guidewire, is advanced through the transeptal sheath. The guide can be advanced, retracted and/or torqued if necessary by manipulation of the mandrel or hypotube 28 to direct the distal opening 22 toward the selected pulmonary vein. The guidewire is then advanced directly into the vein. The guide is adapted to be removed by partially retracting and peeling away from the guidewire.

Deflectable Member

Figure 4:
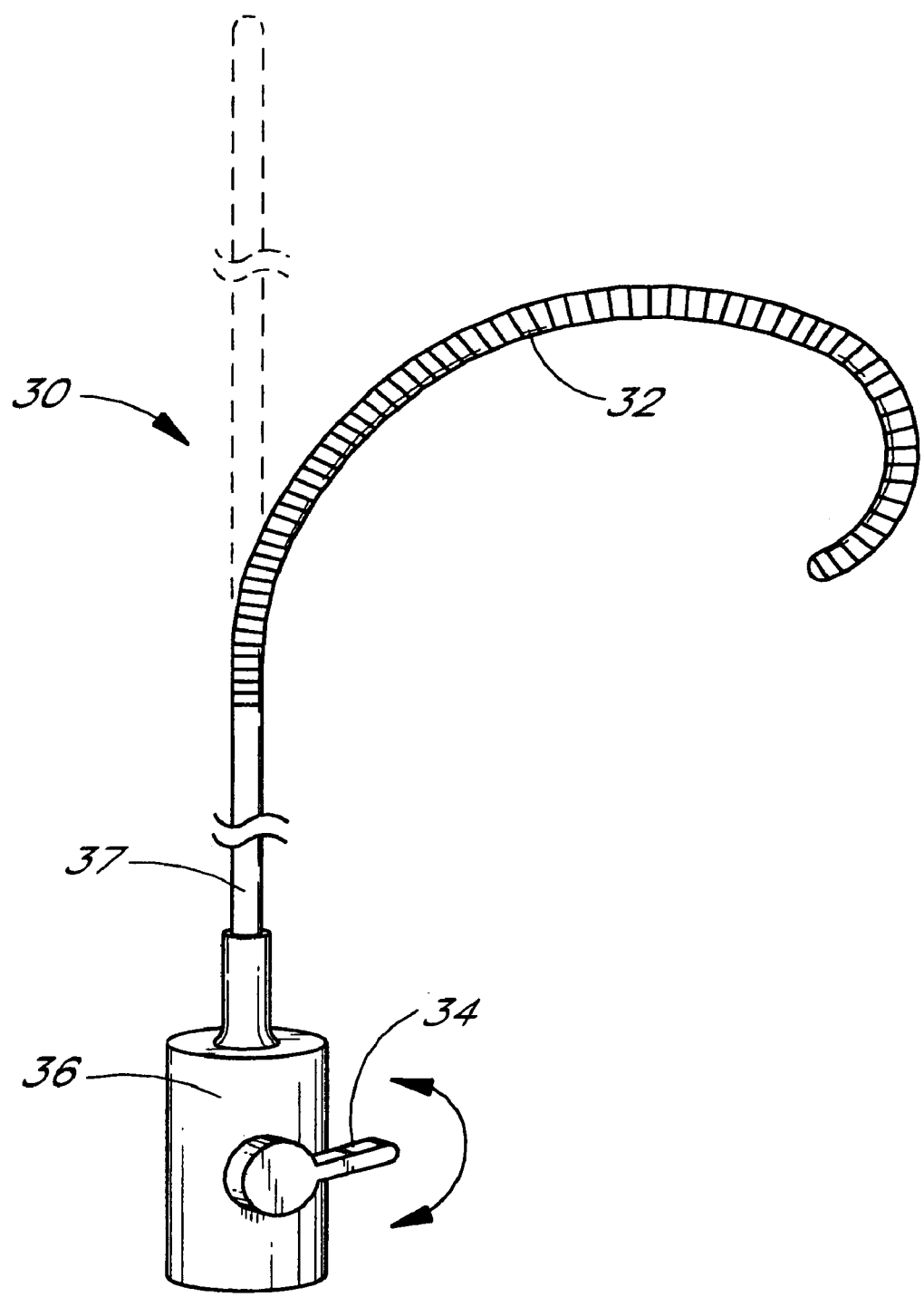
FIG. 4 is a perspective view of a deflectable guidewire in accordance with the present invention.

An embodiment of the positioning system may employ a deflectable member. Devices such as deflectable guidewires are commercially available. With reference to FIG. 4, the deflectable guidewire 30 consists of a tubular wire wound coil 32 surrounding a moveable pullwire (not shown) attached to the coil at the distal end. A flattened member (not shown) is also typically incorporated into the distal lumen. Manipulation of the corewire by operation of the control lever 34 mounted on the handle 36 that is attached to the proximal end 37 of the deflectable guidewire 30 causes the tubular wire wound coil 32 to compress and deflect.

Figure 5:
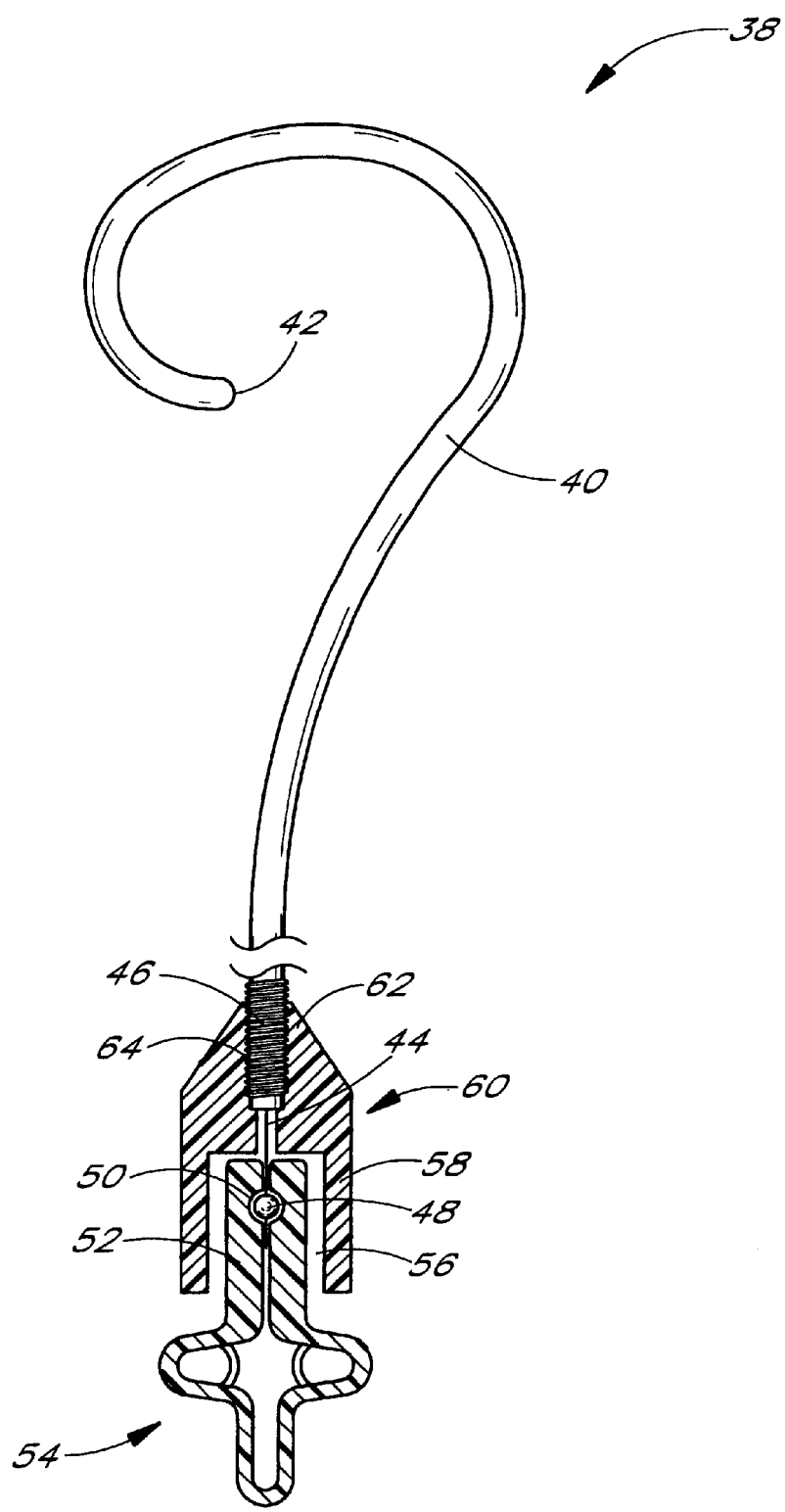
FIG. 5 is a perspective view of another variation of the deflectable guidewire of the present invention having a removable handle.

Another variation of the positioning system of the present invention may employ a deflectable member with a removable handle, as shown in FIG. 5. With reference to FIG. 5, the deflectable guidewire 38 consists of a tubular member 40 made from a wire wound coil surrounding a moveable pullwire. The distal end of the pullwire (not shown) is attached internally to the distal end 42 of the tubular member 40. The proximal end 44 of the pullwire, which extends beyond the externally threaded proximal end 46 of the tubular member 40, has a enlarged stop or ball 48 that is engaged within a recess 50 in the shaft 52 of a pull knob 54. The shaft 52 of the pull knob 54 is slideably engaged within a bore 56 in the proximal region 58 of a handle 60. The distal region 62 of the handle 60 is tapered and includes an internally threaded hole 64 adapted to receive the externally threaded proximal end 46 of the tubular member 40. Pulling on the pull knob 54 causes the tubular member 40 to deflect.

Balloon Anchor Wire

In a preferred variation of the present invention, a balloon anchor wire is placed in the first pulmonary vein in order to serve as a guide for the distal end of the ablation element. An exemplary balloon anchor wire in accordance with the present invention is described in pending provisional application Ser. No. 60/133,610, herein incorporated by reference. The balloon anchor wire consists of a tubular member with a balloon attached to the distal region of the tubular member. The tubular member is fitted over an integral corewire. The corewire extends through the entire length of the tubular member, providing support (e.g., enhancing push force and kink resistance). The distal region of the corewire is tapered providing greater flexibility to the distal region of the tubular member. The distal end of the corewire is bonded to the distal end of the tubular member. The bond between the corewire and the tubular member is airtight, so that the balloon can be inflated. A wire coil may be placed over the distal end of the corewire to help provide support to the corewire and prevent kinking. Preferably, the wire coil protrudes distally from the balloon to aid in atraumatic navigation of vessel branches.

Where the corewire extends only partially through the tubular member, it may terminate anywhere proximal to the balloon. In this variation, the tubular member may comprise distinct proximal, intermediate, and distal regions, in which the corewire terminates in the proximal region of the tubular member. In such case, the proximal region of the tubular member is constructed of a heavier gage polymer, capable of providing the necessary push force and kink resistance, which is provided by the corewire in the continuous corewire design.

The wall of the distal region of the tubular member, which is supported by the integral corewire, is composed of a relatively thick layer (about 0.005" to about 0.015", preferably about 0.010" to 0.012") of low density polymer, such as polyethylene, from which the balloon is formed. In contrast, the wall of the intermediate region of the tubular member, which is also supported by the integral corewire, is composed of a much thinner layer (about 0.001" to about 0.010", preferably about 0.004" to 0.005") of a higher density polymer, such as polyimide. The wall of the proximal region of the tubular member, which is not supported by an underlying corewire, is composed of the same high density polymer as the intermediate region, but of a thickness (about 0.005" to about 0.015", preferably about 0.010" to 0.012") like that of the distal region. The thicker gage high-density polymer construction is necessary in the proximal region absent a continuous corewire, in order to provide sufficient pushing force. In the preferred continuous corewire design, the walls of the tubular member may be constructed out of the same polymeric material of approximately the same gage along the entire length of the balloon anchor wire. Consequently, there may be no distinct regions, having instead only relative proximal and distal regions.

The inside diameter of the tubular member is sufficiently large in relation to the outer diameter of the corewire along the entire length of the tubular member that an inflation lumen is created between the inner wall of the tubular member and the outer surface of the corewire in the intermediate and distal regions of the tubular member. In the proximal region, where no corewire is present, the inflation lumen comprises the entire lumen of the tubular member. In another variation of the balloon anchor wire, a separate inflation lumen may reside within the balloon anchor wire or along the outside of the balloon anchor wire. An inflation medium (i.e., air, saline or contrast) can be passed through the inflation lumen to inflate the balloon.

An over-the-wire variation of the balloon anchor wire of the present invention consists of a tubular member and a distally located balloon. However, a guidewire is slideably engaged within a guidewire passageway that runs longitudinally through the entire length of the balloon anchor wire. An inflation lumen is also present between the inner wall of the tubular member and the outer wall of the guidewire passageway to permit balloon inflation and deflation as described above.

The balloon anchor wire of the present invention has a removable adapter on its proximal end. The shaft of the balloon anchor wire has a proximal end that is inserted into the distal end of the adapter and is engaged therein by a distal O-ring. The distal O-ring can be adjustably tightened and loosened on the proximal end of the shaft by turning the distal knob that is threaded onto the distal end of the adapter. The corewire may exit the proximal end of the adapter. A proximal O-ring engages the corewire. The proximal O-ring can be adjustably tightened and loosened on the corewire by turning the proximal knob that is threaded onto the proximal end of the adapter. A fluid port is in fluid communication with the inflation lumen created between the outer surface of the corewire and the inner wall of the tubular member, thereby allowing inflation and deflation by conventional means of the balloon along the distal region of the balloon anchor wire when the proximal and distal O-rings are tightened.

Linear Ablation Catheter

Exemplary variations of the tissue ablation catheter comprise the ablation assemblies described in pending application Ser. Nos. 09/260,316 and 09/073,907, the disclosures of which are herein incorporated by reference. The ablation assembly includes an irrigated ablation member that is attached to a delivery member in order to access and position the ablation member at the site of the target tissue. The delivery member may take the form of an over-the-wires catheter, wherein the "wires" include first and second guidewires. Preferably, the first guidewire is a balloon anchor wire or a deflectable guidewire. Alternatively, the wires may be engaged by external tracking sleeves. The delivery member comprises an elongated body with proximal and distal end portions. As used herein, the terms "distal" and "proximal" are used in reference to a source of fluid located outside the body of the patient. The elongated body preferably includes a first guidewire lumen, a second guidewire lumen, an electrical lead lumen and a fluid lumen, as described in greater detail below.

Each lumen extends between a proximal port and a respective distal end. The distal ends of the lumens extend through the ablation member, as described in greater detail below. Although the wire, fluid and electrical lead lumens may assume a side-by-side relationship, the elongated body can also be constructed with one or more of these lumens arranged in a coaxial relationship, or in any of a wide variety of configurations that will be readily apparent to one of ordinary skill in the art.

The elongated body of the delivery member and the distally positioned ablation member desirably are adapted to be introduced into the left atrium, preferably through the transeptal sheath. Therefore, the distal end portion of the elongated body and the ablation member are sufficiently flexible and adapted to track over and along the guidewires positioned within the left atrium, and more preferably seated within two of the pulmonary veins that communicate with the left atrium. In an exemplary construction, the proximal end portion of the elongated body is constructed to be at least 30% stiffer than the distal end portion. According to this relationship, the proximal end portion may be suitably adapted to provide push transmission to the distal end portion while the distal end portion and the ablation member are suitably adapted to track through bending anatomy during in vivo delivery of the ablation member into the desired ablation region.

A more detailed construction for the components of the elongated body, which is believed to be suitable for use in transeptal left atrial ablation procedures, is as follows. The elongated body itself may have an outer diameter provided within the range of from about 3 French to about 11 French, and more preferably from about 7 French to about 9 French. Each wire lumen may be adapted to slideably receive a preshaped guiding introducer. Further the wire lumens are adapted to slideably receive a balloon anchor wire, a conventional guidewire and/or a deflectable guidewire ranging from about 0.010" to about 0.038" in diameter, and preferably are adapted for use with guidewires ranging from about 0.018" to about 0.035" in diameter. Where a 0.035" diameter balloon anchor wire is to be used, the balloon anchor wire lumen desirably has an inner diameter of 0.040" to about 0.042". In addition, the fluid lumen desirably has an inner diameter of about 0.019" in order to permit ample irrigation of the ablation member.

The elongated body comprises an outer tubular member that preferably houses an electrical lead tubing, a fluid tubing, a first guidewire tubing and a second guidewire tubing. Each of the tubings extends at least from the proximal end portion of the elongated body to the distal end portion, and at least partially through the ablation member, as described below. The tubings are arranged in a side-by-side arrangement; however, as noted above, one or more of the tubings can be arranged in a coaxial arrangement. Moreover, one or both of the wire tracking means could be located outside of the tubular member, as tubular sleeves. In one mode, the inner tubings are polyimide tubes. Such tubing is available commercially from Phelps Dodge, of Trenton, Ga. The electrical lead and fluid tubings desirably have a 0.019" inner diameter and a 0.023" outer diameter, while the wire tubings are slightly larger, as indicated above. The outer tubular member comprises a thermoplastic, such as, for example, a urethane or vinyl material. A suitable material for this application is Pebax of a grade between 3533 to 7233, and of an outer diameter of about 0.064".

Notwithstanding the specific delivery device constructions just described, other delivery mechanisms for delivering the ablation member to a desired ablation region are also contemplated. For example, while an "over-the-wire" catheter construction was described, other guidewire tracking designs may also be suitable substitutes, such as for example catheter devices known as "rapid exchange" or "monorail" variations wherein the guidewire is only housed within a lumen of the catheter in the distal regions of the catheter. In another example, a deflectable tip design may also be a suitable substitute. The latter variation can also include a pullwire which is adapted to deflect the catheter tip by applying tension along varied stiffness transitions along the catheter's length, as described above.

The proximal end portion of the elongated body terminates in a coupler. In general, any of several known designs for the coupler would be suitable for use with the present tissue ablation device assembly, as would be apparent to one of ordinary skill. For example, a proximal coupler may engage the proximal end portion of the elongated body of the delivery member. The coupler includes an electrical connector that electrically couples one or more conductor leads, which stem from the ablation member and extend through the electrical lead tube, with an ablation actuator. The coupler also desirably includes another electrical connector that electrically couples one or more temperature sensor signal wires to a controller of the ablation actuator.

As known in the art, the ablation actuator is connected to both of the electrical connectors and to a ground patch. A circuit thereby is created which includes the ablation actuator, the ablation member, the patient's body, and the ground patch that provides either earth ground or floating ground to the current source. In the circuit, an electrical current, such as a radiofrequency, ("RF") signal may be sent through the patient between the ablation member and the ground patch, as well known in the art.

The coupler may also include a fluid coupler. The fluid coupler is adapted to be coupled to a source of pressurized fluid (e.g. saline solution) so as to irrigate the ablation member, as described below. The fluid coupler communicates with the fluid tube to supply the ablation member with a source of pressurized fluid.

The ablation member has a generally tubular shape and includes an ablation element. The phrase "ablation element" as used herein means an element that is adapted to substantially ablate tissue in a body space wall upon activation by an actuator. The terms "ablate" or "ablation," including derivatives thereof, are hereafter intended to mean the substantial altering of the mechanical, electrical, chemical, or other structural nature of tissue. In the context of intracardiac ablation applications, "ablation" is intended to mean sufficient altering of tissue properties to substantially block conduction of electrical signals from or through the ablated cardiac tissue. The term "element" within the context of "ablation element" is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type that is adapted to emit energy sufficient to ablate tissue when coupled to and energized by an energy source.

Suitable "energy emitting" ablation elements for use in the present invention may therefore include, for example, but without limitation: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convection or conductive heat transfer, by resistive heating due to current flow, a light-emitting element (e.g., a laser), or an ultrasonic element such as an ultrasound crystal element which is adapted to emit ultrasonic sound waves sufficient to ablate a circumferential region of tissue when coupled to a suitable excitation source. It also is understood that those skilled in the art can readily adapt other known ablation devices for use with the present irrigated ablation member.

In a preferred mode, the ablation element includes a plurality of electrodes that are arranged over a length of the ablation member next to one another (i.e., are arranged in series in the spatial sense). The length from the proximal-most electrode to the distal-most electrode defines an ablation length, which is less than a working length of the ablation element, as described below.

At least one conductor lead connects to the electrodes. The number of conductor leads is desirably equal to the number of electrodes to allow for independent control of each electrode under some modes of operation. Each conductor is a 36 AWG copper wire insulated with a 0.0005" thick polyimide coating. Each conductor exits the electrical lead tube at a point near a corresponding electrode. A distal end of each wire is exposed and is electrically coupled to the corresponding electrode in the manner described below. The proximal end of each conductor lead is connected to the electrical connector on the proximal end of the tissue ablation device assembly.

In one embodiment, an irrigation mechanism may be employed to irrigate the ablation element. The irrigation mechanism is adapted to provide a generally even flow of fluid about each of the electrodes along the length of the ablation member. The irrigation mechanism can be configured to discharge fluid either in a radial direction (i.e., generally normal to the longitudinal axis) or in the longitudinal direction, or in both directions, as illustrated by the below described variations of the ablation member.

The irrigation mechanism desirably includes an inner space defined within a porous, fluid-permeable membrane. The membrane desirably has a generally tubular shape and extends along at least a portion of the ablation member's length; however, the membrane need not be tubular or cover the entire ablation member. The membrane though preferably is arranged to face the target tissue once the ablation element is delivered to and positioned within the particular body space. The membrane has a length, as measured in the longitudinal direction, which is greater than a distance between the proximal-most and distal-most electrodes of the series. The membrane's length is defined between its proximal and distal ends.

The porous membrane includes an inner surface and an outer surface that define the boundaries of a porous wall. The wall is formed of a porous, biocompatible, generally non-compressible material. As used herein, the term "non-compressible" means that the material generally does not exhibit appreciable or sufficient compressibility between its inner and outer surfaces to conform to surface irregularities of the tissue against which the ablation member is placed. The material, however, is sufficiently flexible in the longitudinal direction (i.e., deflectable) so as to track over and along the first and second guidewires positioned within the left atrium, and more preferably seated within two of the pulmonary veins that communicate with the left atrium. In other words, the material of the tubular porous membrane allows it to bend through a winding access path during in vivo delivery of the ablation member into the desired ablation region.

The porous nature of the membrane's material also permits a fluid to pass through the membrane upon the application of a sufficient pressure differential across the membrane. Fluid thus does not freely flow through the membrane. The degree of porosity of the membrane over its length also desirably is uniform. This uniformity coupled with the flow restrictiveness of the material results in the fluid emanating from the member in a generally even flow over the entire membrane outer surface.

Exemplary porous materials suitable for this application include expanded polytetrafluoroethylene (PTFE), porous polyethylene, porous silicon, porous urethane, and tight weaves of Dacron. Such porous materials are formed using conventional techniques, such as, for example by blowing the material or by drilling micro holes within the material. The porosity of the material desirably ranges between about 5 and 50 microns. An acceptable form of the porous PTFE material is available commercially from International Polymer Engineering, of Tempe, Ariz., as Product Code 014-03. It has been found that fluid will pass through this material upon applying a relatively low pressure within the material (e.g., 5 psi). In an exemplary form, the membrane is formed of a tubular extrusion of this material which has an inner diameter of about 0.058" and an outer diameter of about 0.068" for applications involving ablation of myocardial tissue via an arterial or venous access path. For other applications, such as, for example, ablation within small coronary vessels, a significantly smaller diameter size can be used.

The porous membrane is attached to the distal end portion of the delivery member, as noted above. The proximal end of the porous membrane is interposed between the distal end portion of the elongated body and a sealing member. That is, the tubular proximal end of the porous member is placed over the distal end of the elongated body outer tube. The sealing member then is slipped over this assembly and arranged to lie generally above the overlapping sections of the tube and the membrane.

The sealing member desirably is formed of a material similar to or compatible with the material of the elongated body in order to heat-melt bond these two components together. In an exemplary form, the sealing member comprises Pebax of a similar grade used for the outer tube of the elongated body. This bonding process occurs with the proximal end of the porous member positioned between the outer tube distal end and the sealing member.

The porous membrane also desirably includes one or more openings that extend through the wall of the porous membrane. These openings are formed (e.g., punched) on the proximal end of the membrane prior to the bonding procedure, and can take the form of holes or longitudinal slots that extend into the membrane from the proximal end; of course, other shapes of openings can also be used. The similar plastic materials of the seal member and the elongated body outer tube fuse together within these openings and bond under and over the porous material of the membrane during the bonding process. This coupling securely attaches the porous membrane to the distal end portion of the elongated body.

The porous membrane of course can be joined to the distal end portion of the elongated body in any of a variety of other ways well known to those skilled in the art. For instance, the proximal end of the porous membrane can be bonded to the outer tube distal end using a biocompatible adhesive, such as, for example, cyanoacrylate available commercially from Loctite of Rockyhill, Conn., as Part No. 498.

An end cap closes the distal end of the porous membrane. The end cap desirably has a tapering shape that decreases in diameter distally. On its distal end, the end cap includes a port that aligns with the distal end of the first guidewire tube when assembled. The end cap also includes an inner opening defined in part by a collar section. The inner diameter of the collar section is sized to receive the distal ends of the tubings and the outer diameter of the collar is sized to slip within the distal end of the porous membrane.

The end cap desirably is formed of a biocompatible plastic material, such as, for example, urethane or vinyl. In a preferred mode, the end cap is formed of same material that comprises the outer tube of the elongated body, such as, Pebax of a grade between 3533 to 7233, and of an outer diameter of about 0.064".

The end cap and the distal end of the porous membrane desirably are secured together in a similar fashion to that described above. As such, a heat melt bond is formed between a second sealing member and the distal end cap, with the distal end of the porous member being interposed between these elements. The similar plastic materials of the sealing member and the end cap fuse together within openings in the porous membrane at its distal end, as well as over and under the porous membrane. Other bondings can also be used as described above.

The first guidewire tube, the second guidewire tube, the fluid tube, and the lead wire tube each extend within the porous membrane in a longitudinal direction toward the distal end cap.

The electrical lead tube functions as a wiring harness and carries one or more conductors or wires that are attached to the electrodes. The tube extends beyond the distal end portion of the elongated body, through the porous membrane and terminates at a point within the distal end cap. A plug seals the distal end of the electrical lead tube. In an exemplary form, the plug is formed by filling the distal end of the tube with Cyanoaerylate.

The first guidewire tube preferably extends entirely through the ablation member and the distal end cap, and communicates with a distal port formed in the end cap. The distal port is sized to receive a balloon anchor wire over which the elongated body and the ablation member preferably track. The port, thus, allows a first guidewire and preferably a balloon anchor wire to pass through the end cap. In a variation, the first guidewire tube can replace the end cap with the porous membrane attaching directly to the tube. In such an embodiment, the other tube will stop short of the distal end of the ablation member.

The second guidewire tube extends only partially through the ablation member, and communicates with a second, distal port formed in the ablation member located proximal to the proximal end of the ablation element. The second guidewire port is sized to receive a guiding introducer as well as the second guidewire or deflectable guidewire over which the ablation member tracks. The port, thus, allows the guiding introducer and the guidewire to pass out of the ablation member.

The fluid tube defines a pressurizable fluid passageway. The fluid tube extends beyond the distal end portion of the elongated body, through the porous membrane and terminates at a point within the distal end cap next to a distal end of the electrical lead tube. Another plug seals the distal end of the fluid tube. In an exemplary form, the plug is formed by filling the distal end of the tube with Loctite. The tube, however, can terminate proximal of the electrodes but distal of the proximal membrane seal.

The fluid tube includes at least one opening which opens into the inner space defined within the porous membrane. In this manner, the pressurizable fluid passageway or lumen provided by the irrigation tube communicates with the inner space of the ablation member. A single slot is formed near a proximal end of the inner space; however, several slots or holes can be formed along the section of the irrigation tube that extends through the inner space.

A proximal end of the inner space desirably is sealed to prevent a flow of fluid proximally. In the present variation, the distal end of the inner space is also sealed. This allows the pressure within the inner space to be increased to promote fluid weeping through the wall of the porous membrane, as described in greater detail below. The above-described sealing technique provides an adequate seal. In the alternative, a seal can be formed at each location by heat shrinking polyethylene teraphthalate (PET) over the tubes. The proximal seal has an outer diameter of a sufficient size to plug the passage through the elongated body at the distal end of the body and the distal seal has an outer diameter of sufficient size to plug the opening defined by the collar in the distal end cap.

Each electrode in the ablation element comprises a wire coil formed in a helical pattern. The electrodes desirably have identical configurations, and thus, the following description of one is understood to apply equally to all, unless indicated otherwise.

Each coil electrode has a sufficiently large inner diameter to receive tubings, while its outer diameter is sized to fit within the tubular porous membrane. In an exemplary form, each ablation element comprises a 0.005" diameter wire made of a biocompatible material (e.g., stainless steel, platinum, gold-plated nitinol, etc.). The wire is unshielded and is wound in a helical fashion with about a 0.048" inner diameter. The coils are spaced along the lengths of the tubings that extend longitudinally through the porous membrane. In an exemplary mode, each coil has a length, as measured in the longitudinal direction, of about 0.28" and is spaced from an adjacent coil by a distance of about 0.08".

The corresponding conductor wire passes through a hole in the electrical lead tubing and is soldered to the coil with a 95 Ag/5 Sn. The conductor wire can also be electrically connected to the electrodes by other means, such as, for example, by resistant, ultrasonic or laser welding. In addition, the coil and the conductor can be unitary by winding the distal end of the conductor in a helical pattern. Known electrical connectors can also be used to electrically couple the conductor to the corresponding electrode.

The electrodes of the ablation member desirably have sufficient flexibility to bend to track through a venous or arterial access path to an ablation target site. The electrodes can have a variety of configurations as long as they afford similar flexibility. For instance, the electrode can have a tubular or cylindrical shape formed by a plurality of braided wires. The end bands link the ends of the wires together to prevent the braided structure from unraveling. The end bands can also electrically couple the wires together. The bands though are sufficiently narrow so as not to meaningfully degrade the flexibility of the ablation element. Any braided pattern can work, but a "diamond" pattern mesh is preferred. The wires of the braid can either have rectangular ("flat") or rounded cross sections. The wire material can be any of a wide variety of known biocompatible materials (such as those identified above in connection with the coil electrodes). In one mode, the braided electrode can be "wounded" before inserting into the tubular porous membrane. Once inserted, the electrode can be uncoiled to press against the inner surface of the tube. In this manner, the membrane can support the electrode.

An electrode can be constructed where the electrode is formed from a flat wire mesh that has been rolled into an arcuate structure. The structure may have a semi-cylindrical shape; however, the structure can extend through either more or less of an arc. Alternatively, the electrode may have a "fishbone" pattern, wherein the electrode includes a plurality of arcuate segments that extend from an elongated section which generally lie parallel to a longitudinal axis of the ablation member when assembled. The ends of each arcuate segment can be squared or rounded.

An electrode may also be formed in an "arches" pattern. A plurality of arch segments lie in series with two side rails interconnecting the corresponding ends of the arch segments. The arch segments are spaced apart from one another along the length of the electrode. Such embodiments can be formed by etching or laser cutting a tube of electrode material.

Common to all of the electrodes is the ability to flex. The flexibility of these electrodes allows them to bend through tight turns in the venous or arterial access path without collapsing. The electrodes also have low profiles so as to minimize the outer diameter of the ablation member. Fluid can also pass radially through the electrodes. Other types of electrode designs that exhibit these features can also be used. For example, the electrode can be formed in a manner resembling a conventional stent by etching or laser cutting a tube. The electrode also need not extend entirely about the longitudinal axis of the ablation member; the electrode can be generally flat and positioned on only one side of the catheter. A serpentine shape would provide such a flat electrode with the desired flexibility. However, in order for the ablation member to be less orientation sensitive, each electrode desirably extends through at least 180 degrees about the longitudinal axis of the ablation member. Accordingly, the foregoing electrode designs are merely exemplary of the types of electrodes that can be used with the present ablation member.

Although the following variations of the irrigation ablation member are described as including a coiled electrode, it is understood that any of foregoing designs, as well as variations thereof, can be used as well with these devices.

The tissue ablation device assembly also desirably includes feedback control. For instance, the ablation member can include one or more thermal sensors (e.g., thermocouples, thermisturs, etc.) that are provided to either the outer side or the inside of the porous membrane. Monitoring temperature at this location provides indicia for the progression of the lesion. The number of thermocouples desirably equals the number of electrodes so as to enhance the independent control of each electrode. If the temperature sensors are located inside the porous membrane, the feedback control may also need to account for any temperature gradient that occurs across the membrane.

The sensors placed on the exterior of the porous member may also be used to record electrogram signals by reconnecting the signal leads to different input port of the signal-processing unit. Such signals can be useful in mapping the target tissue both before and after ablation.

In the one embodiment, the temperature sensors each comprise an annular thermocouple that is positioned about the outer side of the porous membrane. In this location, the thermocouple lies on the outside of the membrane where it can directly contact the tissue-electrode interface. The thermocouple is isolated from direct metal-to-metal electrical contact with the electrodes because the thermocouples are separated by the porous membrane. Thus, separate insulation is not necessary.

The thermocouples desirably are blended into the outer surface of the ablation member in order to present a smooth profile. Transition regions formed by either adhesive or melted polymer tubing, "smooth out" the surface of the ablation member as the surface steps up from the porous member outer surface to the thermocouple surface.

Signal wires extend proximally from the thermocouples to the electrical connector on the proximal end of the tissue ablation device assembly. In the illustrated mode, the wires are shielded and extend into the porous membrane and then into the electrical lead tube. These wires can be routed proximally in other manners. For instance, the wires can form a braided structure on the exterior of the ablation member and then be pulled together and routed proximally along the side of the elongated body. The wires can also be routed proximally inside one or more tubes that extend parallel to and are attached to the elongated body. The wires can also be sewn into the wall of the outer tubing of the elongated body. These represent a few variations on various ways of routing the thermocouple wires to the proximal end of the tissue ablation device assembly.

In use, the electrical and fluid connectors of the proximal coupler are connected to the ablation actuator and the pressurized fluid source, respectively. A conventional grounding patch or other grounding device is placed against the patient.

The ablation member can be constructed in other forms while obtaining the above-noted advantages. For instance, the ablation member can include a different shaft construction from that described above. The balloon anchor wire and guidewire tubes may extend longitudinally through the ablation member positioned within a structure of braided wires. Each of the wires is insulated, and the wires desirably are woven in a diamond-like pattern.

The braided structure desirably includes at least an inner or an outer coating of a plastic material so as to define a pressurizable fluid passageway. An inner layer and an outer layer of polymer are laminated over the braid structure to define a generally fluid-impermeable structure. The polymer layers stop at the distal end of the elongated body though. The braided structure continues distally to form a support structure for the ablation member. Fluid can pass through the uncoated braided structure.

The braided structure supports the electrodes. The electrodes are spaced along the length of the braided structure to define the linear ablation element. One of the wires from the braid is connected to a corresponding electrode. Any of the above-described connectors can be used to electrically couple an unshielded end of the conductor wire to the corresponding electrode.

A spacer may be placed between adjacent electrode pairs to prevent fluid from flowing through a corresponding section of the braided structure not covered by an electrode. The spacers can be formed of a polymer or an epoxy attached directly to the braided structure. The absence of a spacer, however, provides a fluid flow between the electrodes that may be beneficial in some applications.

The porous membrane covers the electrodes supported by the braided structure. A proximal end of the porous membrane is secured to the distal end of the elongated body, as defined by the distal end of the laminate structure. The proximal end of the porous membrane can be attached in any of the above-described manners.

Similarly, the distal end of the porous membrane is attached to an end cap. The end cap includes an elongated collar that receives a distal end of the braided structure. The distal end of the porous membrane extends over the collar and is secured thereto in any of the above-described manners.

The ablation member can also include one or more thermocouples. The thermocouples are attached to the porous membrane in the manner described above. The thermocouple wires extend through the membrane and through the braided structure, and are routed proximally through the inner lumen of the braided structure that defines the pressurizable fluid passageway. The proximal ends of the thermocouple wires are connected to an electrical connector of a proximal coupler.

Another variation of the ablation member involves an extruded shaft including a plurality of lumens. The shaft can be formed of Pebax or another suitably flexible thermoplastic. The shaft includes four lumens: a first guidewire lumen, a second guidewire lumen, a fluid lumen, and an electrical lead lumen. Although the lumens are arranged in a side-by-side arrangement, two or more of the lumens can have a coaxial arrangement. Plugs close the distal ends of the electrical lead lumen and the fluid lumen.

The shaft supports the electrodes. The electrodes are spaced along the length of the shaft to define the linear ablation element. A conductor lead extends through the wall of the shaft from the electrical lead lumen at a point near the corresponding electrode. Any of the above-described connectors can be used to electrically couple an unshielded end of the conductor wire to the corresponding electrode. Each of the electrical leads is connected to the proximal coupler located at the proximal end of the tissue ablation device assembly.

The porous membrane covers the electrodes supported by extrusion shaft. A proximal end of the porous membrane is securely sealed about the outer surface of the shaft, and the distal end of the porous member is securely sealed about the shaft at a point proximal of the distal end of the shaft. The ends of the porous membrane can be attached to the shaft in any of the above-described manners.

This variation of the ablation member can also include one or more thermocouples. The thermocouples are attached to the porous membrane in the manner described above. In the illustrated variation, the thermocouple wires extend through the membrane and through a hole in the shaft that opens into the electrical lead lumen, and are routed proximally through the lumen. The proximal ends of the thermocouple wires are connected to an electrical connector of a proximal coupler.

The shaft also includes an opening located just distal of the annular attachment of the proximal end of the porous member to the shaft. The opening extends from the fluid lumen and opens into an inner space defined within the porous membrane. In this manner, fluid can flow from the fluid lumen and into the inner space so as to pressurize the inner space before passing through the membrane in the manner described above.

In each of the above-described variations of the ablation member, the porous membrane covers the electrodes. The porous membrane, however, can lie inside or beneath the electrodes while still providing an even flow past each of the electrodes. This modification can be incorporated into each of the variations described above. Thus, for example, the porous membrane located between the electrodes and the braided structure. The porous membrane lies atop the braided structure. The electrodes are placed about the braided structure and the porous membrane. The ablation member desirably includes a reduced diameter section in which the electrodes reside to maintain a generally uniform profile along the distal end of the tissue ablation device assembly. Spacers can also be positioned within this section to lie between adjacent pairs of electrodes. As noted above, such spacers prevent fluid from flowing through the porous membrane at locations other than those about which an electrode is located. The ablation member, however, can be configured without spacers so as to provide a fluid flow between adjacent electrodes.

Further variations of the ablation member may include a design where the distal end of the ablation member is open; however, it desirably has a tapering diameter. The smaller diameter permits some pressure to build within the fluid passageway such that at least some of the fluid within the passageway emanates radially through the braided structure and the porous membrane, and across the electrodes. The distal end also can be rounded to ease tracking through a venous or arterial access path.

The braided structure form supports the porous membrane over its entire length. Other support can also be used. For example, internal or external rings can be spaced at various points along the length of the porous membrane to support further the membrane. In the alternative, a mandrel can also be used for this purpose. A proximal end of the mandrel can be embedded with the laminate structure and project in the distally.

Alternatively, a fluid delivery tube is located within the braided structure and can be moved by its proximal end located outside the patient, so as to vary the location of the distal end of the tube. The distal end of the tube includes one or more openings which allow fluid to be delivered by the tube into the pressurizable passageway. By moving the distal end of the fluid tube, the amount of fluid flowing across a particular electrode can be varied. To further promote this effect, the fluid tube can include baffles located on the proximal and distal sides of the fluid openings. These baffles enhance a radial flow of the fluid through porous membrane. Of course, these features can also be incorporated into several of the other variations described above.

The foregoing describes variations of an ablation member used to form linear ablations within a body space. The ablation member can be incorporated into a variety of delivery devices so as to locate and position the ablation member within the body space. At least one of the proximal and distal ends of the ablation member desirably is connected to the delivery device. That end is maneuverable within the body space by manipulating a proximal end of the delivery device.

In order to add the proper positioning of the ablation element within the porous membrane, the catheter tip and the porous membrane desirably include indicia which correspond to each other once the distal end of the ablation member has been advanced to a point positioning it within the membrane. For in vivo applications, such indicia can take the form of radiopaque markers positioned at corresponding locations on the catheter and the porous membrane (or another location on the sheath).

Positioning System

Figure 6:
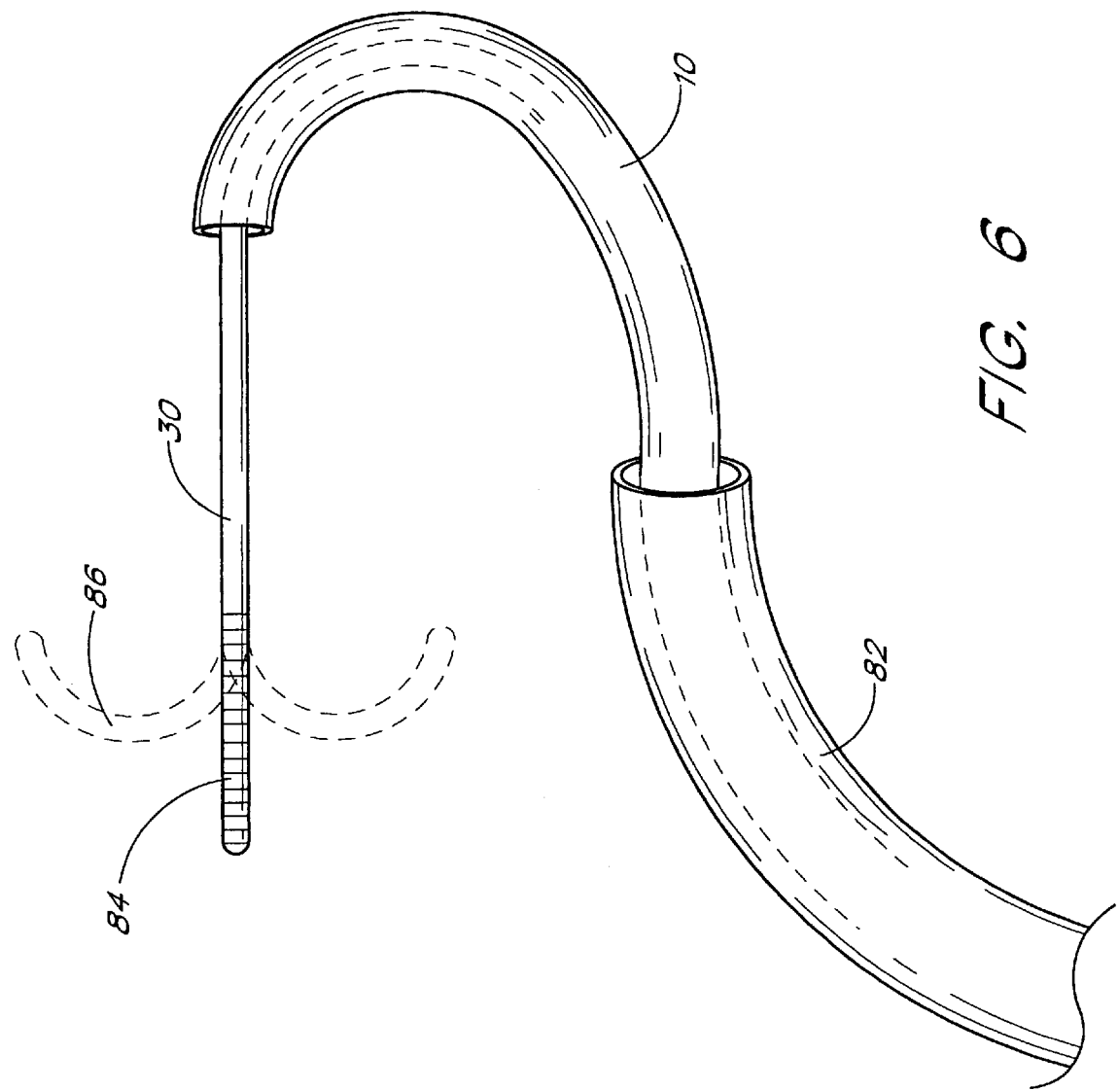
FIG. 6 is a schematic view of a variation of the positioning system of the present invention showing a deflectable guidewire slideably engaged within a preshaped guiding introducer slideably engaged within a transeptal sheath.

The positioning system of FIG. 6 illustrates the relationship among a transeptal sheath 82, a preshaped guiding introducer 10 and a deflectable guidewire 30. The deflectable guidewire 30 is shown passing through and slideably engaged within the preshaped guiding introducer 10. The distal end 84 of the deflectable guidewire 30 is aimed by the preshaped guiding introducer 10 toward a predetermined pulmonary vein. The distal end 84 can be deflected 86 (shown in shadow) to steer the guidewire into the first or second pulmonary vein and/or to anchor the guidewire within the pulmonary vein. In one variation, the guidewire is a balloon anchor wire having an inflatable balloon at the distal end of the guidewire. The balloon anchor wire may be advanced through the preshaped guiding introducer 10 and into a pulmonary vein. Subsequently, the balloon is inflated and the guiding introducer 10 is removed, by retraction over the anchored balloon, by peeling away, where the guiding introducer has a longitudinal slit, or by any other method known in the art.

Figure 7:
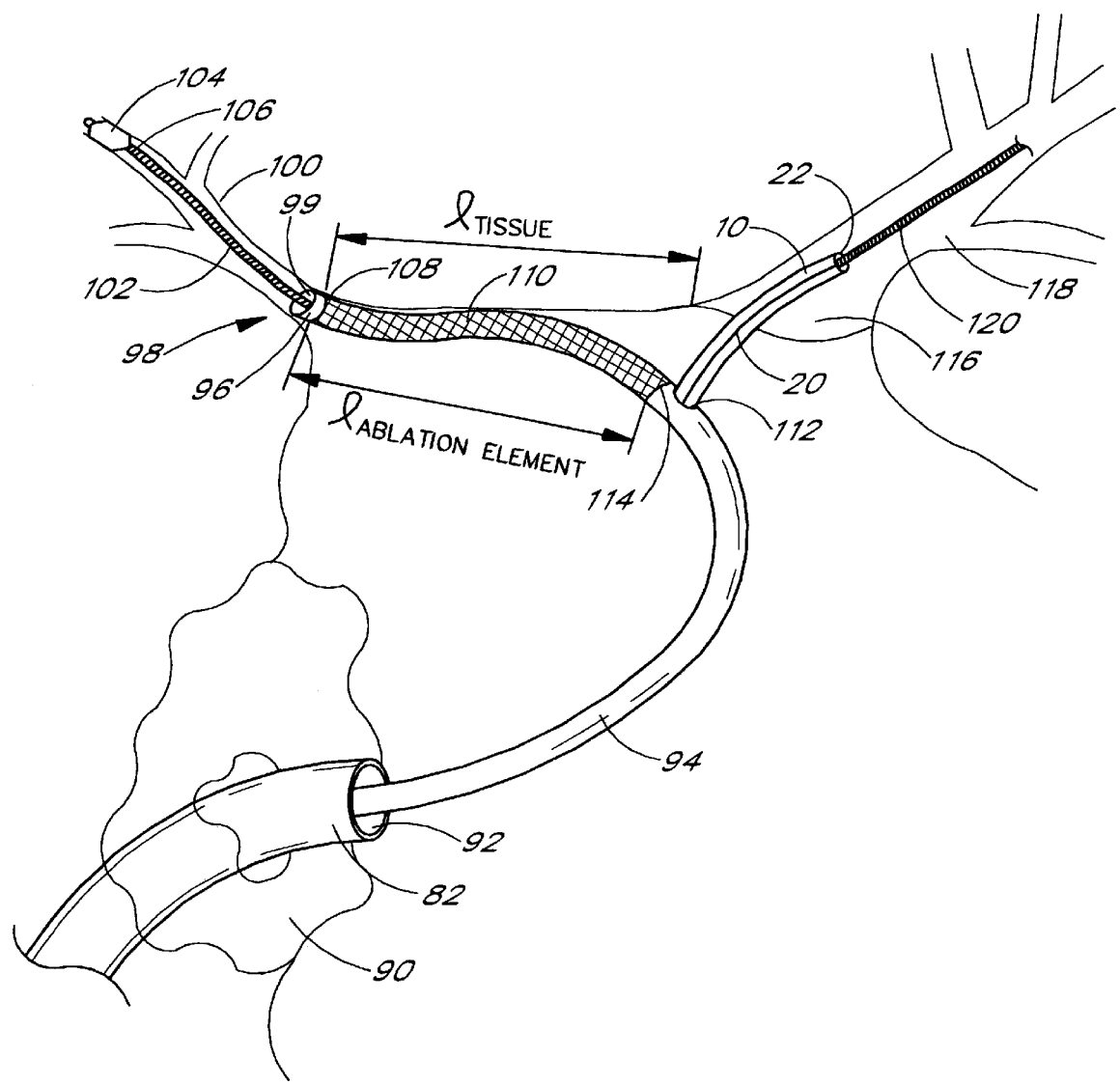
FIG. 7 is a schematic view of a variation of the catheter positioning system of the present invention in situ, showing the distal end of the ablation catheter tracking over a balloon anchor wire into the first pulmonary vein and a preshaped guiding introducer extending from a second guidewire port in the ablation catheter and directing a second guidewire into the second pulmonary vein.

A preferred variation of the positioning system of the present invention is shown in situ in FIG. 7. The transeptal sheath 82 traverses the atrial septum 90 that separates the right and left atria. The distal end 92 of the transeptal sheath opens into the left atrium. Emerging from the transeptal sheath and slideably engaged therein is the ablation catheter 94. The distal end 96 of the ablation catheter 94 is shown engaging a first ostium 98 of a first pulmonary vein 100. A balloon anchor wire 102, having a balloon 104 on its distal end 106 is slideably engaged within the ablation catheter 94, exiting the catheter through the first guidewire port 99. The balloon anchor wire 102 may have been positioned within the first pulmonary vein as described above, or as detailed in pending U.S. Provisional application Ser. No. 60/133,610, herein incorporated in its entirety by reference thereto. The balloon 104 is located within the first pulmonary vein 100 and inflated so as to anchor the ablation catheter 94 in position within the first ostium 98 of the first pulmonary vein 100. Consequently, the distal end 108 of a linear ablation element 110 is secured against the atrial wall at a location where the first pulmonary vein 100 extends from the atrium.

A preshaped guiding introducer 10, having a longitudinal slit 20 to permit peel-away removal, is shown emerging from a second guidewire port 112 in the ablation catheter 94. The second guidewire port 112 is located proximal to the proximal end 114 of the ablation element 110. The distal orifice 22 of the preshaped guiding introducer is manipulated to point toward, or optionally reside within, the second ostium 116 of the second pulmonary vein 118. A second guidewire 120, slideably engaged within the preshaped guiding introducer 10, is positioned within the second pulmonary vein 118. By tracking distally over the preshaped guiding introducer 10 and/or the guidewire 120, the proximal end 114 of the ablation element 110 can be positioned and secured at a location where the second pulmonary vein 118 extends from the atrium. The preshaped guiding introducer 10 can optionally be removed after the guidewire 120 has been positioned within the pulmonary vein 118. Removal of the guiding introducer 10 may be accomplished by retraction and/or peeling away as described above.

Figure 8:
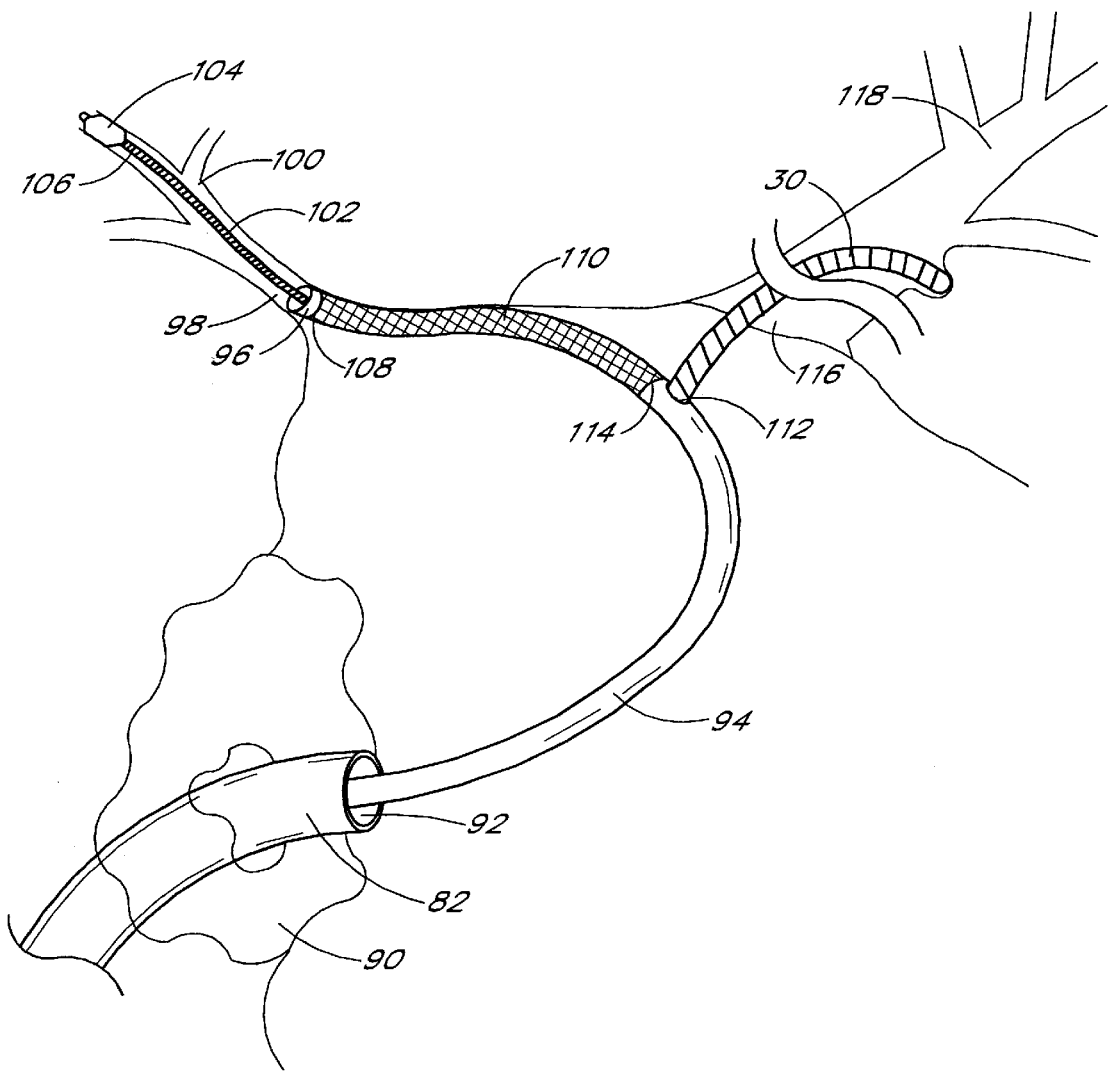
FIG. 8 is a schematic view of another variation of the catheter positioning system of the present invention in situ, showing the distal end of the ablation catheter tracking over the balloon anchor wire into the first pulmonary vein and a deflectable guidewire extending from a second guidewire port in the ablation catheter and cannulating the second pulmonary vein.

Another variation of the positioning system of the present invention is shown in situ in FIG. 8. Again, the transeptal sheath 82 traverses the atrial septum 90 that separates the right and left atria. The distal end 92 of the transeptal sheath opens into the left atrium. Emerging from the transeptal sheath and slideably engaged therein is the ablation catheter 94. The distal end 96 of the ablation catheter 94 is shown engaging a region of tissue, for example, a first ostium 98, where the first pulmonary vein 100 extends from the atrium. A balloon anchor wire 102, having a balloon 104 on its distal end 106 is slideably engaged within the ablation catheter 94. The balloon 104 is located within the first pulmonary vein 100 and inflated so as to anchor the ablation catheter 94 in position within the first ostium 98 of the first pulmonary vein 100. Consequently, the distal end 108 of the linear ablation element 110 is secured at a location where the first pulmonary vein 100 extends from the atrium.

A deflectable guidewire 30 is shown emerging from the second guidewire port 112 in the ablation catheter 94. The deflectable guidewire 30 is slideably engaged within the ablation catheter 94 and the distal end 122 is adapted to be steerable by manipulating a pullwire (not shown) at the proximal end of the guidewire. Preferably, the deflectable guidewire 30 is advanced into the second pulmonary vein 118 and anchored therein by deflection of the distal end 122. By tracking over the deflectable guidewire 30, the proximal end 114 of the ablation element 110 can be positioned and secured at a location, for example, the second ostium 116, where the second pulmonary vein 118 extends from the atrium. The deflectable guidewire 30 may have been positioned within the second pulmonary vein using a preshaped guiding introducer as described above.

Method of Using the Positioning System of the Present Invention

A patient diagnosed with atrial fibrillation due to perpetually wandering reentrant wavelets originating from an arrhythmogenic origin or focus in the left atrium and more particularly in a pulmonary vein may be treated with a tissue ablation device assembly of the present invention by using the assembly to form a longitudinal conduction block along a path of the wall tissue of the pulmonary vein that either includes the arrhythmogenic origin or is between the origin and the left atrium. In the former case, the conduction block destroys the arrhythmogenic tissue at the origin as it is formed through that focus. In the latter case, the arrhythmogenic focus may still conduct abnormally, although such aberrant conduction is prevented from entering and affecting the atrial wall tissue due to the intervening conduction block.

In positioning the ablation element at the ablation region, an introducer sheath is first positioned within the left atrium according to a transeptal access method, which will be described in more detail below, and through the fossa ovalis. The right venous system is first accessed using the "Seldinger" technique, wherein a peripheral vein (such as a femoral vein), is punctured with a needle and the puncture wound is dilated with a dilator to a size sufficient to accommodate an introducer sheath. An introducer sheath that has at least one hemostatic valve is seated within the dilated puncture wound while relative hemostasis is maintained. With the introducer sheath in place, a guiding catheter is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guiding catheter until it punctures the fossa ovalis. A separate dilator can also be advanced with the needle through the fossa ovalis to prepare an access port through the septum for seating the transeptal sheath. Thereafter, the transeptal sheath replaces the needle across the septum and is seated in the left atrium through the fossa ovalis, thereby providing access for object devices through its own inner lumen and into the left atrium.

It is also contemplated that other left atrial access methods may be utilized for using the positioning system of the present invention. In one alternative variation, a "retrograde" approach may be used, wherein a guiding catheter is advanced into the left atrium from the arterial system. In this variation, the Seldinger technique is employed to gain vascular access into the arterial system, rather than the venous system, such as at a femoral artery. The guiding catheter is advanced retrogradely through the aorta, around the aortic arch, into the left ventricle, and then into the left atrium through the mitral valve.

After gaining access to the left atrium, a balloon anchor wire or other guidewire is advanced into a first predetermined pulmonary vein. This is generally done through a preshaped guiding introducer which is coaxial within the transeptal sheath seated in the fossa ovalis, such as for example, the preshaped guiding introducers described in FIGS. 1–3, or by using a deflectable guidewire or catheter such as those described in FIGS. 4–5, or those disclosed in U.S. Pat. No. 5,575,766 to Swartz. Alternatively, the guidewire may have sufficient stiffness and maneuverability in the left atrial cavity to unitarily select the desired pulmonary vein distally of the transeptal sheath seated at the fossa ovalis.

The guidewire, balloon anchor wire or deflectable guidewire may be preloaded within the guiding introducer or inserted into the proximal end of the guiding introducer after it has been positioned. Subsequently, the guidewire is advanced through the guiding introducer until the distal end exits the distal orifice of the guiding introducer, the guidewire being aimed by the guiding introducer toward the first pulmonary vein.

The balloon anchor wire or other guidewire is then advanced into the first pulmonary vein to a suitable anchoring position. The fixed corewire variation of the balloon anchor wire is directly advanced into the first pulmonary vein. Alternatively, where the over-the-wire variation is used, the guidewire is advanced into the pulmonary vein first and then the tubular member with the distal balloon follows, tracking over the guidewire and into the pulmonary vein. Anchoring of the guidewire is accomplished in either case by inflating the balloon to a predetermined air pressure or volume of a saline/contrast mixture. Where a deflectable guidewire is employed, the distal region of the guidewire is deflected after it is positioned well within the pulmonary vein. Effective anchoring is tested by gently tugging on the guidewire. If the guidewire is not sufficiently anchored, the balloon is deflated or the deflection released, and the wire is advanced further into the pulmonary vein or one of its branches. Inflating and/or deflecting, testing and repositioning are performed in this manner until the guidewire is sufficiently anchored. If necessary the balloon anchor wire or deflectable guidewire may be advanced into a different branch of the first pulmonary vein to find a secure anchoring position.

Once the guidewire is securely anchored, the shaped guiding introducer may be retracted back through the transeptal sheath and removed. The peel-away variety may be partially retracted and then peeled away from the guidewire. Alternatively, where the proximal end of the balloon anchor wire has a removable Y-adapter (inflation/deflation hub), the Y-adapter is removed by releasing the pressure on the balloon, loosening the distal and proximal O-ring knobs on the adapter, and sliding the adapter off the balloon anchor wire. Care must be taken not to displace the balloon on the distal end of the anchor wire when removing the adapter from the proximal end of the anchor wire. Once the Y-adapter has been removed, the guiding introducer may be withdrawn completely by sliding it off the proximal end of the balloon anchor wire.

The ablation catheter, which is adapted to slideably engage the balloon anchor wire or other guidewire, is then slid over the proximal end of the guidewire. Once the ablation catheter is advanced past the proximal end of the balloon anchor wire, the Y-adapter is reattached and the balloon is re-inflated. Similarly, where a deflectable guidewire with a removable handle, like that illustrated in FIG. 5, is employed, the handle is reattached once the ablation catheter is advanced past the proximal end of the deflectable guidewire. The distal end of can then be deflected again to anchor the guidewire. The user should gently tug on the guidewire to insure that it is still securely anchored in the first pulmonary vein.

The ablation catheter is then advanced over the guidewire, through the transeptal sheath, and continuing until the distal end of the ablation catheter, including the distal end of the ablation element, engages the first pulmonary vein ostium. A combination of pushing and pulling alternatively on both the guidewire and the ablation catheter may be employed to facilitate advancement of the ablation catheter. In a variation of the method, a stylet may be placed inside the ablation catheter to further assist in advancing it along the guidewire toward the first pulmonary vein ostium. Once the distal end of the ablation catheter engages the first pulmonary vein ostium and is securely seated therein, the proximal portions of the ablation catheter, including the proximal end of the ablation element, are further advanced into the left atrium, causing the ablation catheter to prolapse against the atrial wall. If a stylet was used inside the ablation catheter to facilitate advancement and positioning of the ablation catheter, retracting the stylet now may permit the catheter to conform more readily to the atrial wall.

Where a second guidewire is being employed to facilitate positioning of the proximal end of the ablation element, the guidewire is advanced into a second pulmonary vein prior to prolapsing the ablation catheter against the atrial wall. This is preferably accomplished by advancing a preshaped guiding introducer, which was preloaded within the ablation catheter, distally through the second guidewire passageway in the ablation catheter until the curved distal end of the guiding introducer emerges from the second guidewire port, located proximal to the proximal end of the ablation element. The guiding introducer can then be advanced, retracted and/or torqued in such a manner as to cause the distal orifice of the guiding introducer to point toward the second ostium of the second pulmonary vein. In one variation, the guiding introducer can be advanced into the pulmonary vein. The second guidewire is then advanced through the guiding introducer into the pulmonary vein. The deflectable guidewire may be used alone within the second guidewire passageway or may be slideably engaged within a guiding introducer as described above.

Once the guidewire is in place within the second pulmonary vein, the proximal end of the ablation element is advanced more accurately toward the second pulmonary vein ostium by tracking along the guidewire. As described above a stylet may be employed within the ablation catheter to push the proximal end of the ablation element toward the second ostium of the second pulmonary vein.

Delivery of RF energy to the endocardial tissue of the pulmonary vein is commenced once the ablation member is positioned at the desired ablation region. Good contact between the ablation element and the underlying tissue facilitates the creation of a continuous transmural lesion. RF energy from the ablation actuator is delivered to electrodes via electrical leads. The ablation actuator desirably includes a current source for supplying a RF current, a monitoring circuit, and a control circuit. The current source is coupled to the linear ablation element via a lead set, and to a ground patch. The monitor circuit desirably communicates with one or more sensors (e.g., temperature or current sensors) which monitor the operation of the linear ablation element. The control circuit is connected to the monitoring circuit and to the current source in order to adjust the output level of the current driving the electrodes of the linear ablation element based upon the sensed condition (e.g., upon the relationship between the monitored temperature and a predetermined temperature set point).

At the same time, conductive fluid, such as saline, is directed into the fluid coupler and through the fluid lumen. In some instances, it may be desirable to begin to apply positive fluid pressure even before RF ablation is commenced in order to prevent blood accumulation in or on the ablation member.

In one variation, the saline passes through openings in the fluid tubing to an inner space within the porous membrane. When the pressure within the inner space reaches a predetermined pressure, the fluid weeps out of the porous membrane. The fluid can be uniformly distributed along the longitudinal length of the ablation element because the fluid does not immediately flow through the porous membrane, but instead remains within the inner space until the predetermined pressure is reached. This provides for both a uniform flow of fluid through the length of the porous membrane and a uniform flow of RF energy along the ablation element. That is, the porous membrane diffuses the saline across each individual electrode, as well as across the array of electrodes. While the conductive fluid or saline is used to create a uniform conductive path between the electrodes and the target tissue, the saline can be alternatively or additionally utilized to cool the ablation electrodes. The fluid flows both through the helical coil of the ablation element and between the plurality of ablation elements of the ablation member, thereby facilitating the cooling of the electrodes by the fluid. The bath of saline may possibly cool the electrodes so as to be capable of delivering high levels of current or be capable of longer durations to produce deeper lesions.

Once a lesion has been formed along the target length, the ablation catheter may be repositioned and additional lesions formed.

Figure 9:
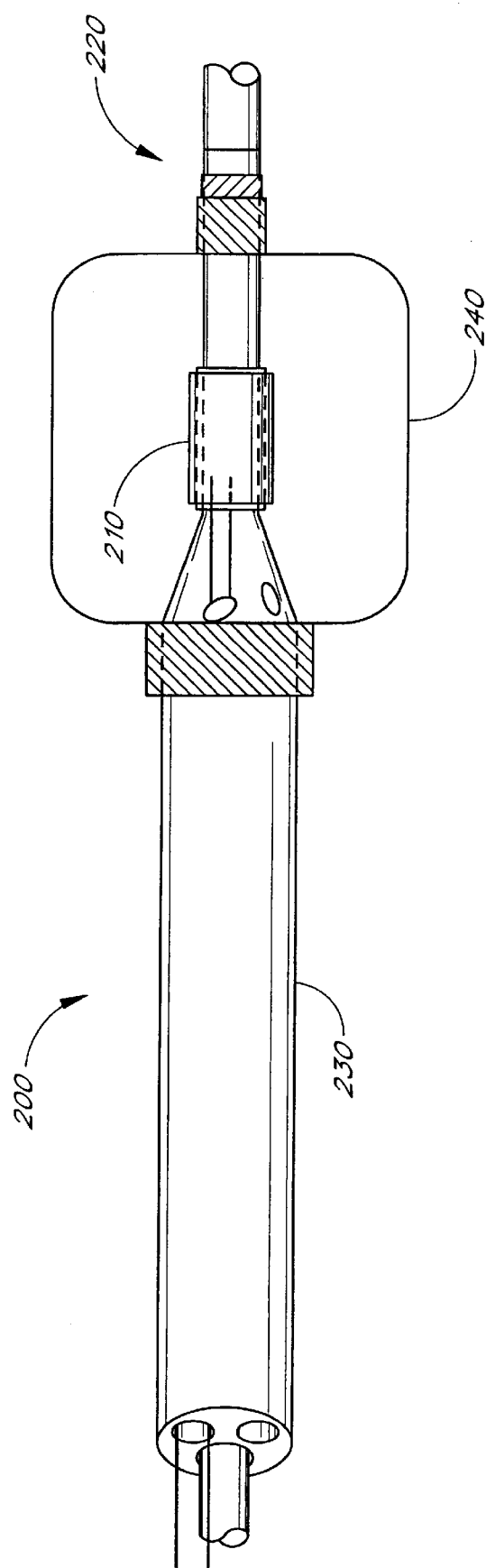
FIG. 9 is a longitudinal cross-sectional view of an anchor device in accordance with a preferred mode of the present invention, showing an over-the-wire catheter with an ultrasound ablation element positioned along the distal end portion within an expandable member.

In accordance with another mode of the ablation catheter, an ultrasound sonically couples with the outer skin of the balloon in a manner that forms a circumferential conduction block in a pulmonary vein as follows. FIG. 9 shows an ablation catheter 200 in accordance with this mode of the present invention. An ultrasound transducer 210 is located along the distal end portion 220 of the catheter shaft 230 within an inflatable balloon 240. Initially, the ultrasound transducer 210 is believed to emit its energy in a circumferential pattern that is highly collimated along the transducer's length relative to its longitudinal axis L. The circumferential band therefore maintains its width and circumferential pattern over an appreciable range of diameters away from the source at the transducer 210. Also, the balloon 240 is preferably inflated with fluid that is relatively ultrasonically transparent, such as, for example, degassed water. Therefore, by actuating the transducer 210 while the balloon 240 is inflated, the circumferential band of energy is allowed to translate through the inflation fluid and ultimately sonically couple with a circumferential band of balloon skin that circumscribes the balloon 240. Moreover, the circumferential band of balloon skin material may also be further engaged along a circumferential path of tissue which circumscribes the balloon 240, such as, for example, if the balloon 240 is inflated within and engages a pulmonary vein wall, ostium, or region of atrial wall. Accordingly, where the balloon 240 is constructed of a relatively ultrasonically transparent material, the circumferential band of ultrasound energy is allowed to pass through the balloon skin and into the engaged circumferential path of tissue such that the circumferential path of tissue is ablated.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the embodiments variously shown to be "guidewire" tracking variations for delivery into a left atrium and around or within a pulmonary vein may be modified to instead incorporate a deflectable/steerable tip instead of guidewire tracking and are also contemplated. Moreover, all assemblies described are believed useful when modified to treat other tissues in the body, in particular other regions of the heart, such as the coronary sinus and surrounding areas. Further, the disclosed assemblies may be useful in treating other conditions, wherein aberrant electrical conduction may be implicated, such as for example, heart flutter. Indeed, other conditions wherein catheter-based, directed tissue ablation may be indicated, such as for example, in the ablation of fallopian tube cysts. Accordingly, it should be understood that various applications, modifications and substitutions may be made of equivalents without departing from the spirit of the invention or the scope of the following claims.

What is claimed is:

1. A positioning system for guiding a catheter to a location where a pulmonary vein extends from an atrium, comprising:

a transseptal sheath having a distal opening, the transseptal sheath being adapted for traversing an atrial septum;

a first guidewire adapted for slidable advancement through the distal opening in the transseptal sheath, the first guidewire having a deflectable distal portion for steering the first guidewire to a first pulmonary vein; and a catheter adapted for advancement over the first guidewire and into the atrium the catheter being independently advancable through the sheath distal opening.

2. The positioning system of claim 1, wherein the first guidewire comprises a wire wound coil surrounding a moveable pullwire, and wherein a proximal end of the first guidewire is adapted to facilitate manipulation of the pullwire, such that manipulation of the pullwire causes deflection of the distal portion of the first guidewire.

3. The positioning system of claim 1, wherein the first deflectable guidewire is integral with the catheter.

4. The positioning system of claim 3, wherein the catheter further comprises proximal and distal ends and a moveable pullwire attached to the distal end of the catheter, and wherein the proximal end of the catheter is adapted to facilitate manipulation of the pullwire, such that manipulation of the pullwire causes deflection of the distal end of the catheter.

5. The positioning system of claim 1, wherein the catheter further comprises an electrode element.

6. The positioning system of claim 5, wherein the electrode element comprises a mapping electrode.

7. The positioning system of claim 5, wherein the electrode element comprises an ablation electrode.

8. The positioning system of claim 5, wherein the electrode element comprises both a mapping electrode and an ablation electrode.

9. The positioning system of claim 5, wherein the electrode element is an RF ablation element.

10. The positioning system of claim 1, wherein the catheter further comprises an ablation element.

11. The positioning system of claim 10, wherein the ablation element comprises a microwave ablation element.

12. The positioning system of claim 10, wherein the ablation element comprises a cryogenic ablation element.

13. The positioning system of claim 10, wherein the ablation element comprises a thermal ablation element.

14. The positioning system of claim 10, wherein the ablation element comprises a light-emitting ablation element.

15. The positioning system of claim 10, wherein the ablation element comprises an ultrasound transducer.

16. The positioning system of claim 10, wherein the ablation element is adapted to form a linear lesion.

17. The positioning system of claim 10, wherein the ablation element is adapted to form a circumferential lesion.

18. The positioning system of claim 10, wherein the ablation element is adapted to form a circumferential lesion at the location.

19. The positioning system of claim 1 wherein the catheter further comprises a side port located proximal to the ablation element.

20. The positioning system of claim 19 further comprising a second guidewire adapted for advancement through the ablation catheter and out through the side port for insertion into a second pulmonary vein for engagement therein.

21. The positioning system of claim 20 further comprising a guiding introducer that is advancable through the ablation catheter and out the side port for facilitating the advancement of the second guidewire into the second pulmonary vein.

22. The positioning system of claim 20, wherein the second guidewire is deflectable for facilitating advancement out the side port and into the second pulmonary vein.

* * * * *